(12) United States Patent
Badehi et al.

(10) Patent No.: US 6,673,014 B2
(45) Date of Patent: Jan. 6, 2004

(54) NONINVASIVE METHODS AND APPARATUSES FOR MEASURING THE INTRAOCULAR PRESSURE OF A MAMMAL EYE

(75) Inventors: Avner Pierre Badehi, Doar Na Harei Yehuda (IL); Raphael Klein, Los Altos, CA (US); Arieh Glazer, Mevaseret Tsion (IL)

(73) Assignee: Itonix, Inc., Los Altos, CA (US)

( * ) Notice: Subject to any disclaimer, the term of this patent is extended or adjusted under 35 U.S.C. 154(b) by 0 days.

(21) Appl. No.: 09/972,819

(22) Filed: Oct. 5, 2001

(65) Prior Publication Data

US 2003/0078486 A1 Apr. 24, 2003

(51) Int. Cl.$^7$ ................................................ A61B 3/16
(52) U.S. Cl. ........................ 600/398; 600/402; 600/400
(58) Field of Search .............................. 73/80; 600/399, 600/400, 401, 402, 403, 404, 405, 561

(56) References Cited

U.S. PATENT DOCUMENTS

| | | | |
|---|---|---|---|
| 2,519,681 A | 8/1950 | Mages | 600/398 |
| 3,049,001 A | 8/1962 | MacKay | 600/405 |
| 3,070,997 A | 1/1963 | Papritz | 600/405 |
| 3,105,381 A | 10/1963 | Collette | 73/800 |
| 3,150,520 A | 9/1964 | MacKay | 600/398 |
| 3,150,521 A | 9/1964 | MacKay | 600/398 |
| 3,181,351 A | 5/1965 | Stauffer | 600/401 |
| 3,192,765 A | 7/1965 | Keiper | 600/398 |
| 3,338,089 A | 8/1967 | Coombs | 600/405 |
| 3,498,717 A | 3/1970 | Kumagai | 356/5.02 |
| 3,538,754 A | 11/1970 | Grolman et al. | 600/401 |
| 3,545,260 A | 12/1970 | Lichtenstein et al. | 600/400 |
| 3,585,849 A | 6/1971 | Grolman | 600/401 |

(List continued on next page.)

OTHER PUBLICATIONS

Sheikh, et. al., "Detection of Intraocular Pressure Change in the Eye Using Sonoelastic Doppler Ultrasound," Ultrasound in Medicine and Biology, vol. 20, No. 8, pp. 751–758, Aug. 1994.

Jack M. Hamelink, "IOP Measurement Using Sonic Excitation and Laser Velocimetry," Ph.D. Dissertation Thesis, Department of Metallurgy, Mechanics and Materials Science, Michigan State University, 1978.

Robert D. Blevis, Ph.D., "Formulas for Natural Frequency and Mode Shape," Van Nostrand Reihold Company (Publisher), 1979, pp. 291–335.

Werner Soedel, Professor, "Vibrations of Shells and Plates," Marcel Dekker, Inc. (Publisher), 1981, pp. 124–131.

(List continued on next page.)

*Primary Examiner*—Max F. Hindenburg
*Assistant Examiner*—Jonathan Foreman
(74) *Attorney, Agent, or Firm*—Sheppard Mullin Richter & Hampton LLP

(57) ABSTRACT

Noninvasive methods and apparatuses measuring the intraocular pressure (IOP) of the eye using vibratory excitation are disclosed. Prior art methods teaches that the natural frequencies of the eye vary as a function of the IOP, with each natural frequency being zero at zero IOP. The present invention recognizes that the eye has different and separate classes of natural frequencies that vary as function of the IOP, which have non-zero values for a zero value of IOP, and which have curves that extrapolate to negative IOPs to obtain zero values of frequency. Preferred methods and apparatuses of the present invention measure a first natural frequency of this class at an unknown IOP value, and thereafter compare it to one or more known values of the first natural frequency measured at corresponding known IOPs to estimate value of the unknown IOP. Preferred embodiments include measuring one or more additional natural frequencies.

51 Claims, 7 Drawing Sheets

U.S. PATENT DOCUMENTS

| | | | | |
|---|---|---|---|---|
| 3,613,666 A | | 10/1971 | Hobbs | 600/402 |
| 3,690,158 A | | 9/1972 | Lichtenstein et al. | 600/400 |
| 3,763,696 A | | 10/1973 | Krakau | 600/402 |
| 3,882,718 A | | 5/1975 | Kriebel | 600/401 |
| 3,948,248 A | | 4/1976 | Zuckerman et al. | 600/457 |
| 4,089,329 A | | 5/1978 | Couvillon, Jr. et al. | 600/398 |
| 4,193,401 A | * | 3/1980 | Marinello | 604/290 |
| 4,621,644 A | | 11/1986 | Eilers | 600/405 |
| 4,747,296 A | | 5/1988 | Feldon et al. | 73/1.62 |
| 4,759,370 A | | 7/1988 | Kozin et al. | 600/398 |
| 4,886,066 A | | 12/1989 | Ingalz et al. | 600/398 |
| 4,907,595 A | * | 3/1990 | Strauss | 600/452 |
| 4,928,697 A | | 5/1990 | Hsu | 600/402 |
| 4,930,507 A | | 6/1990 | Krasnicki et al. | 600/402 |
| 4,945,913 A | | 8/1990 | Krasnicki et al. | 600/400 |
| 5,051,931 A | | 9/1991 | Cheu et al. | 600/558 |
| 5,109,852 A | | 5/1992 | Kaye et al. | 600/398 |
| 5,148,807 A | | 9/1992 | Hsu | 600/402 |
| 5,179,953 A | | 1/1993 | Kursar | 600/399 |
| 5,217,015 A | | 6/1993 | Kaye et al. | 600/405 |
| 5,251,627 A | | 10/1993 | Morris | 600/398 |
| 5,293,532 A | | 3/1994 | Marshall | 351/225 |
| 5,375,595 A | | 12/1994 | Sinha et al. | 600/402 |
| 5,396,888 A | | 3/1995 | Massie et al. | 600/405 |
| 5,469,848 A | | 11/1995 | Toleman | 600/438 |
| 5,865,742 A | | 2/1999 | Massie | 600/405 |
| 5,982,297 A | | 11/1999 | Welle | 340/870.16 |
| 6,030,343 A | | 2/2000 | Chechersky et al. | 600/399 |
| 6,037,704 A | | 3/2000 | Welle | 310/339 |
| 6,053,866 A | | 4/2000 | McLeod | 600/300 |
| 6,083,161 A | | 7/2000 | O'Donnell, Jr. | 600/405 |

OTHER PUBLICATIONS

W. O. Wray, et al., "A Mechanical Model for Radial Keratotomy: Toward a Predictive Capability," Journal of Biomechanical Engineering, vol. 116, Feb. 1994, pp. 56–61.

Kenneth C. Henderson, "A Nonlinear Modal Frequency Response Analysis of the Pre–stressed Human Eye by the Finite Element Method: A research topic in non–contacting tonometry," Department of Electrical Engineering, University of Rochester, Rochester New York, (M.S. Thesis) May 1995.

Kenneth S. Bhella, "Intraocular Pressure Measurement Using Resonance Detection," Department of Electrical Engineering, University of Rochester, Rochester New York, (M.S. Thesis) May 1995.

* cited by examiner

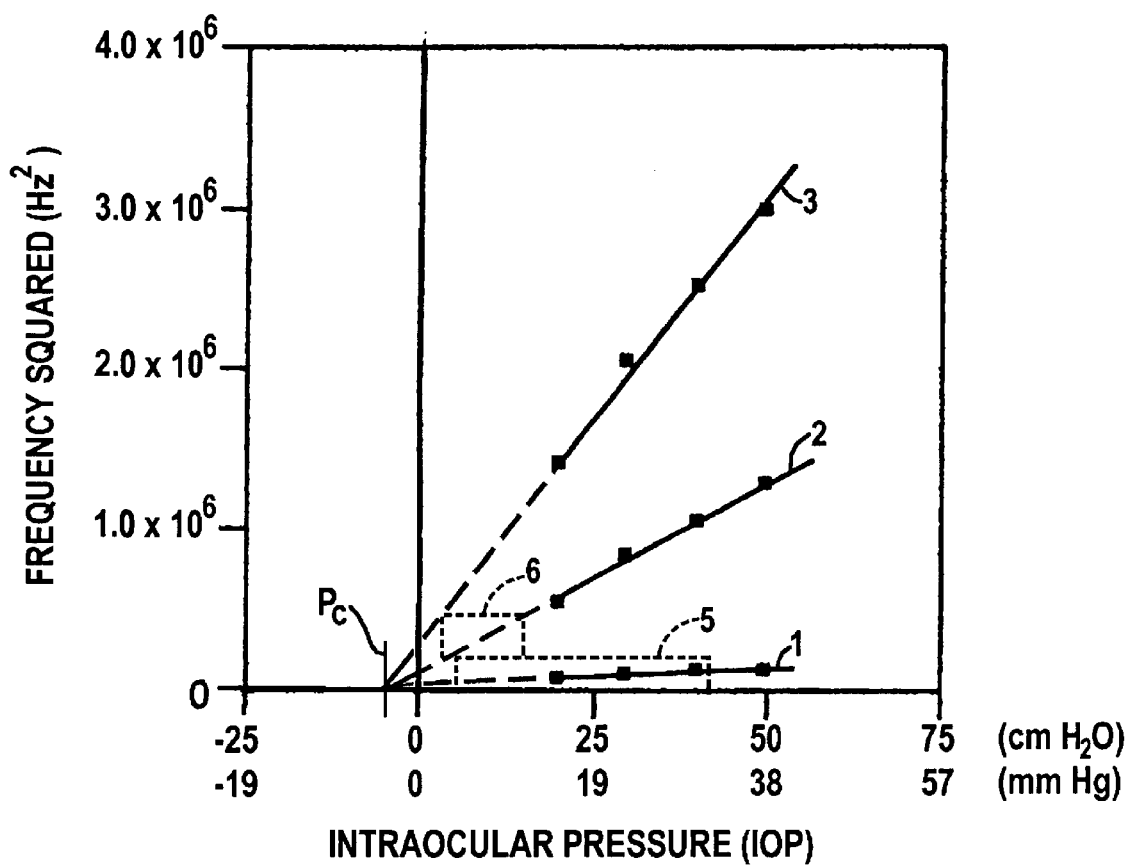
FIG._1

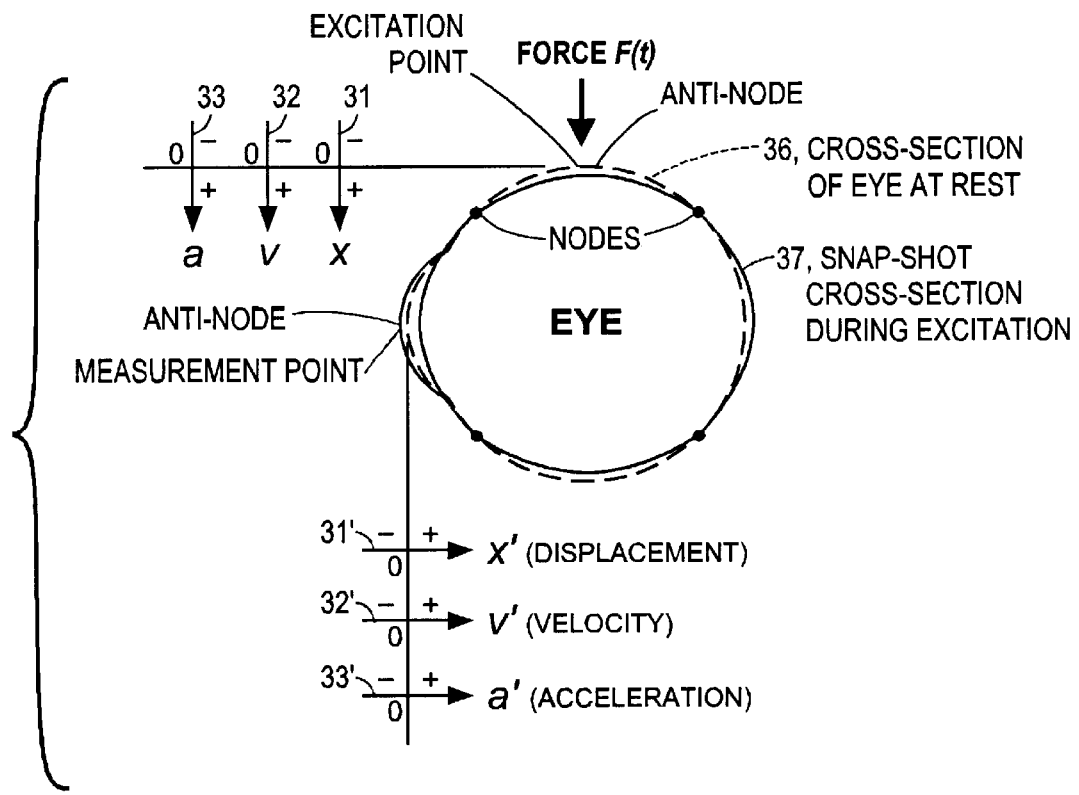
FIG._2
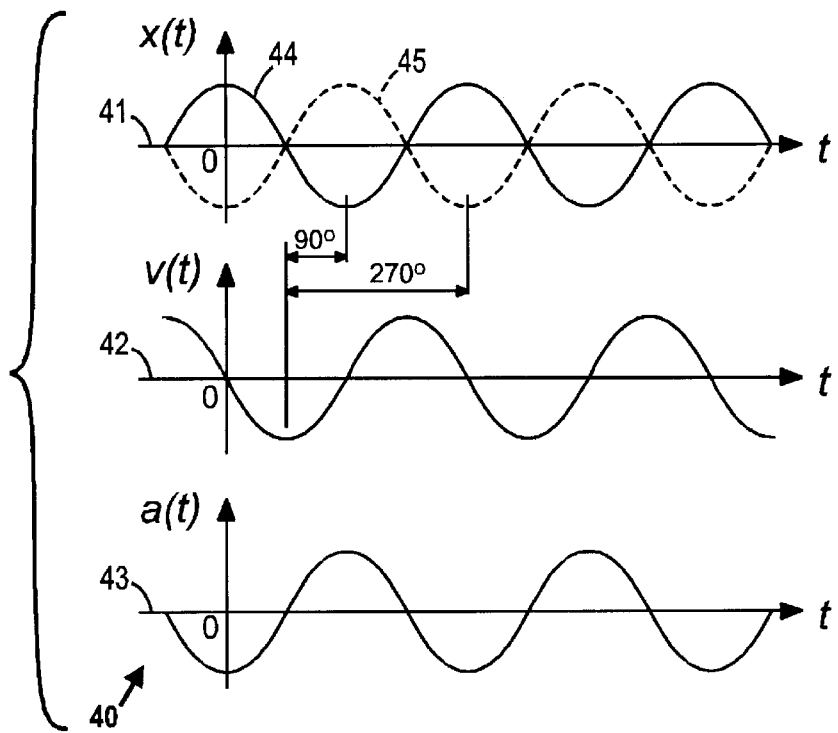
FIG._3

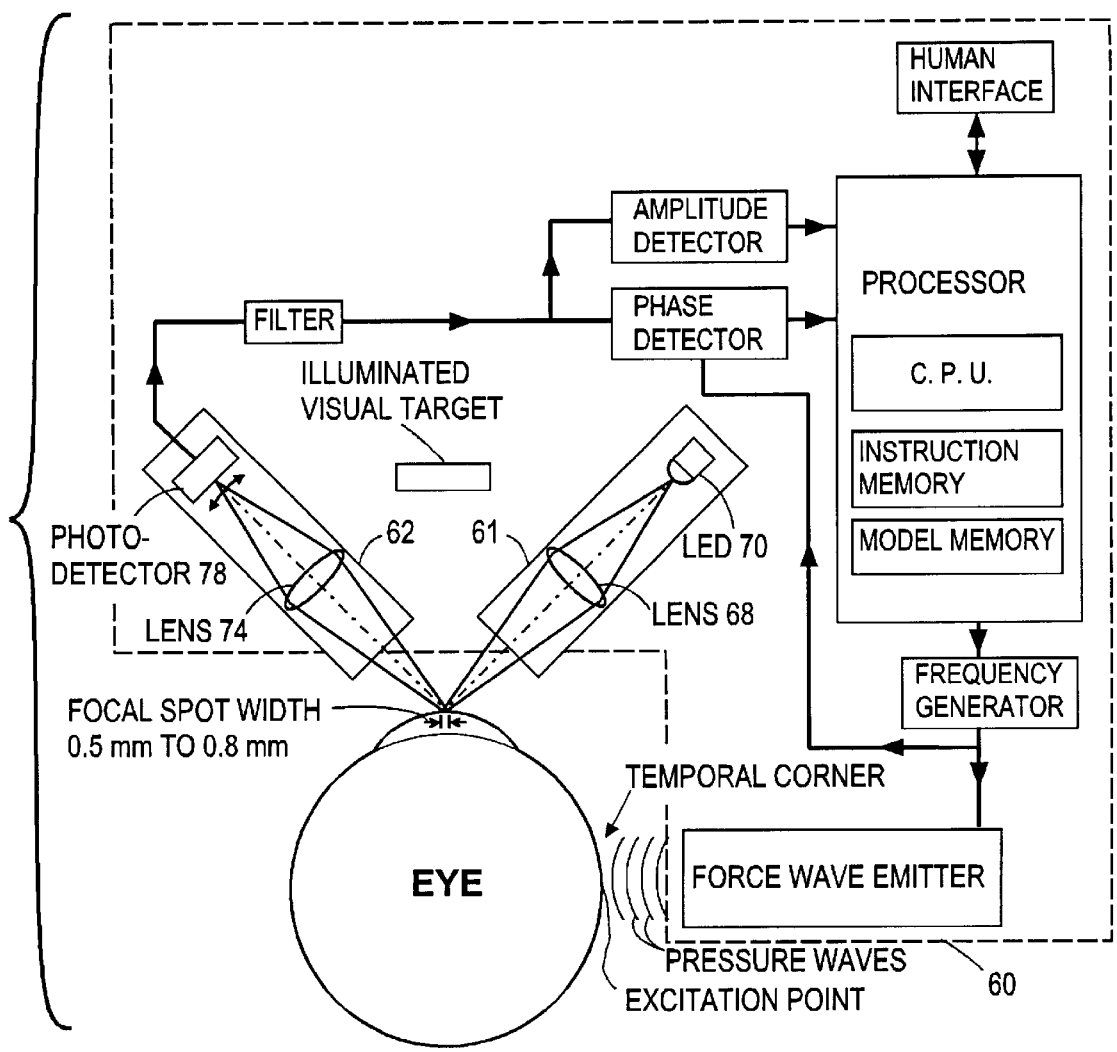
FIG._4

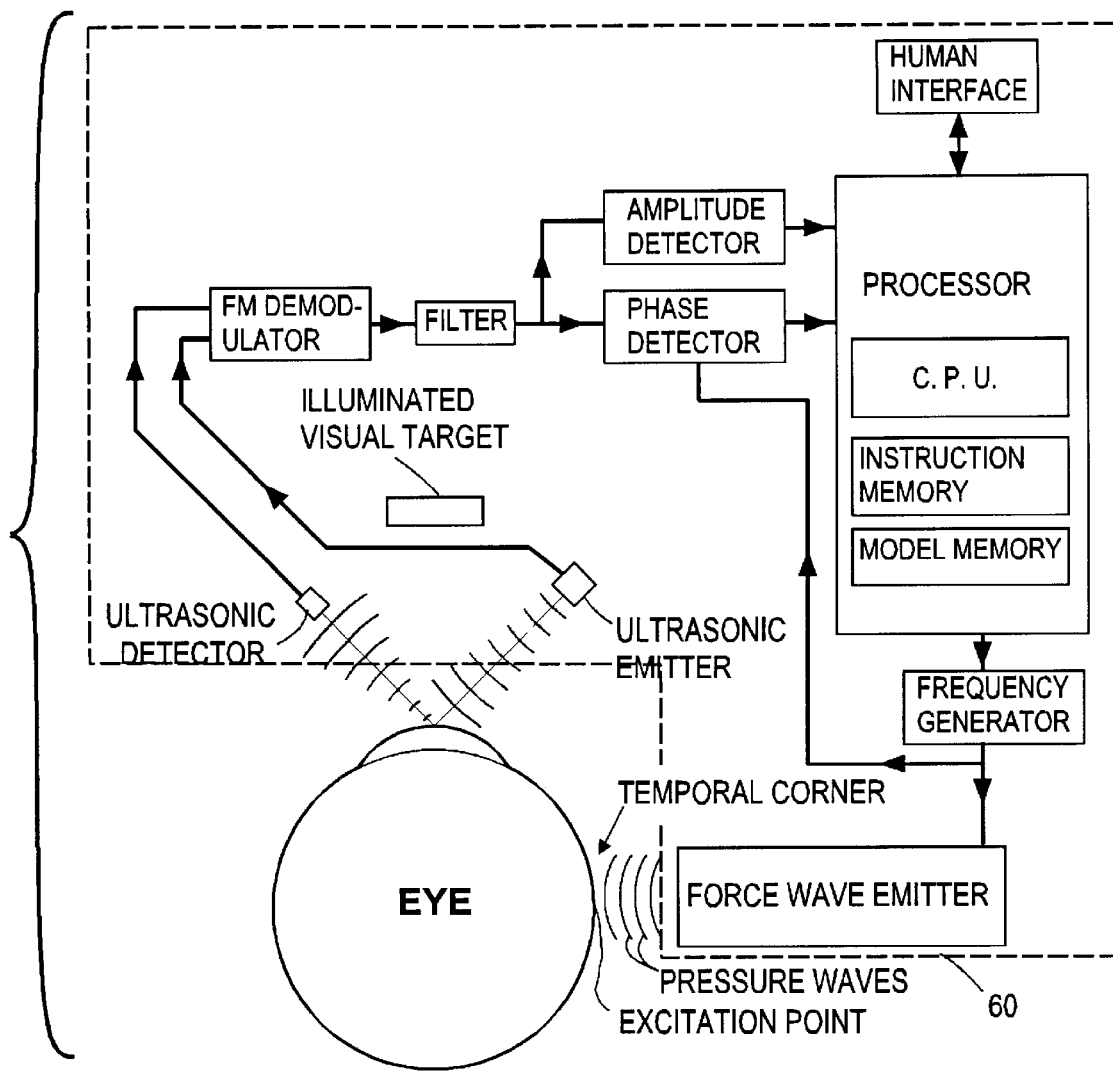
FIG._5

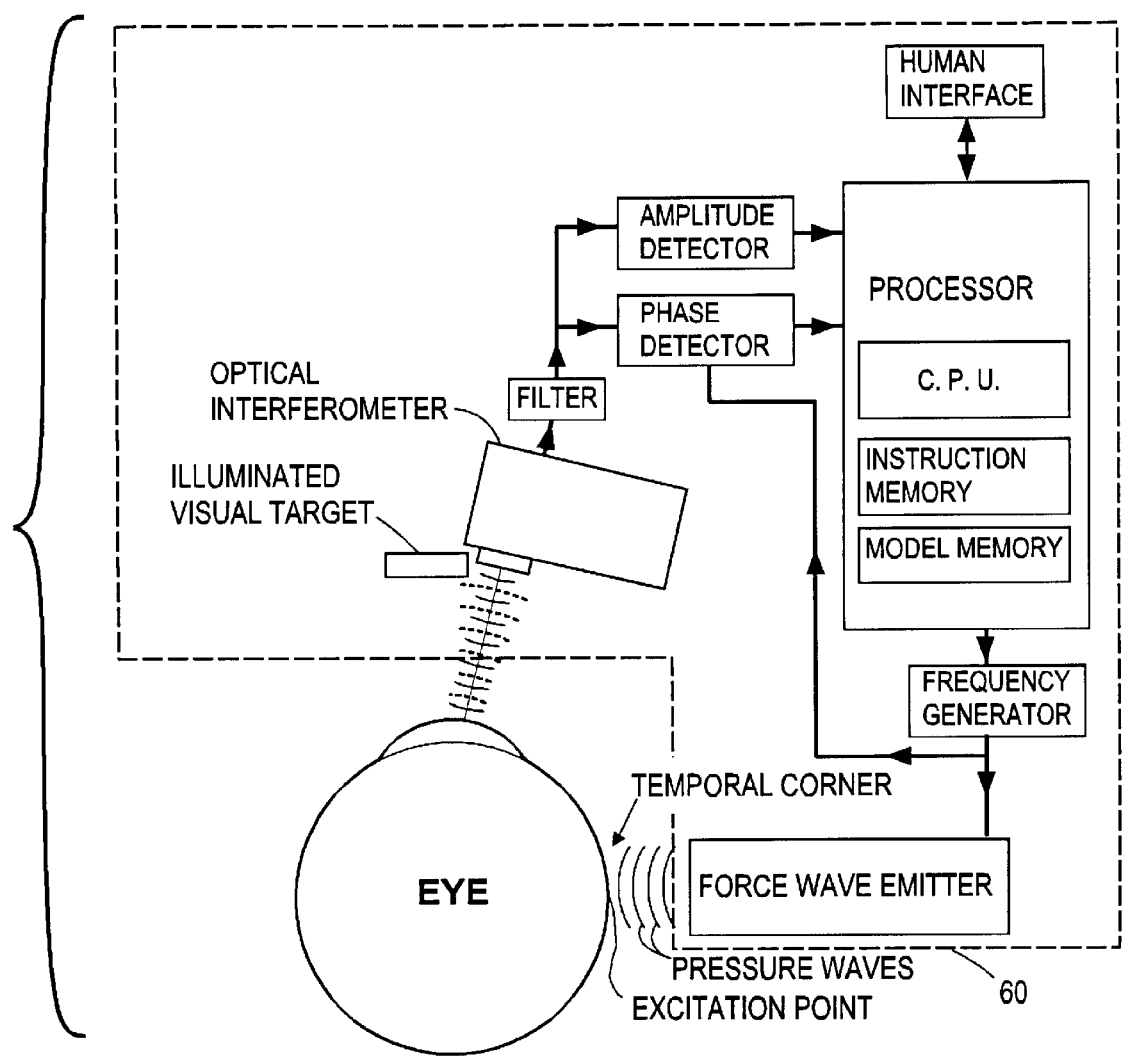
FIG._6

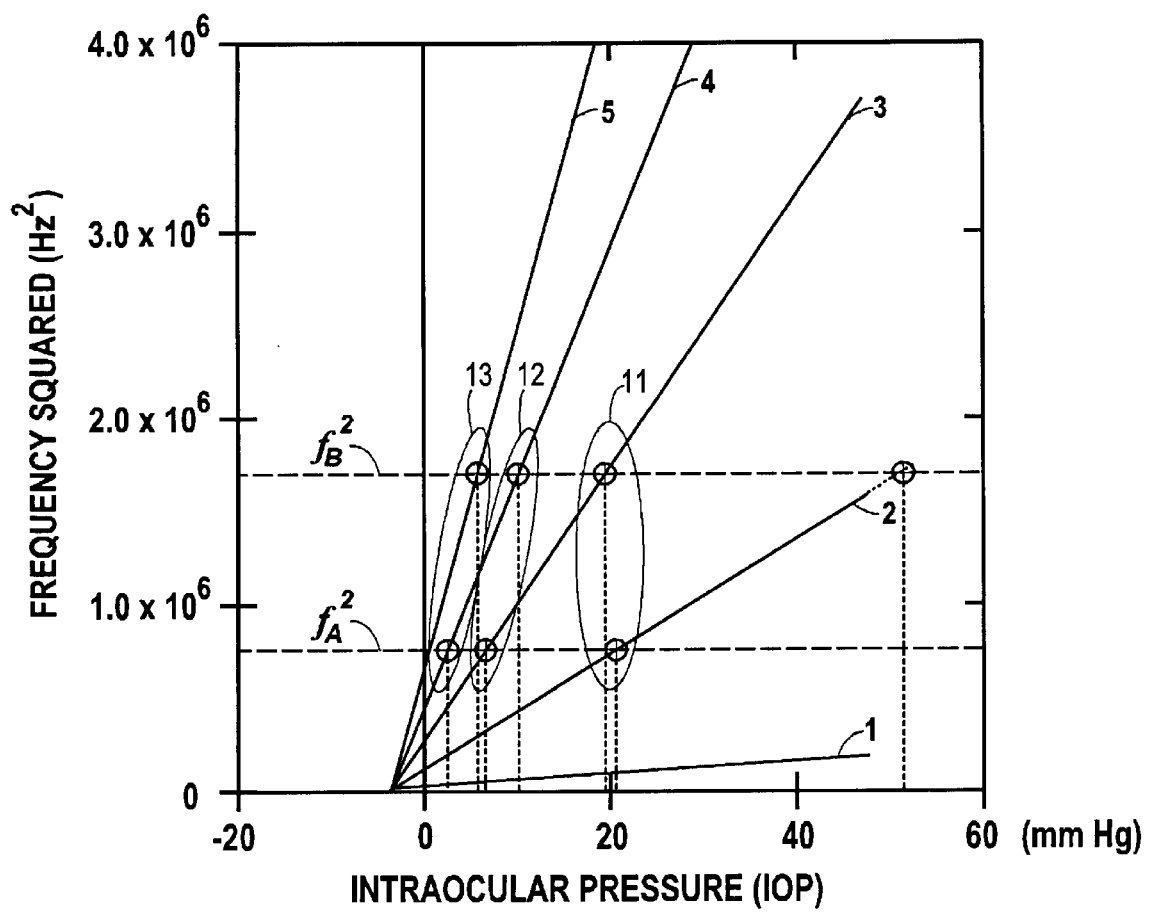
FIG._7

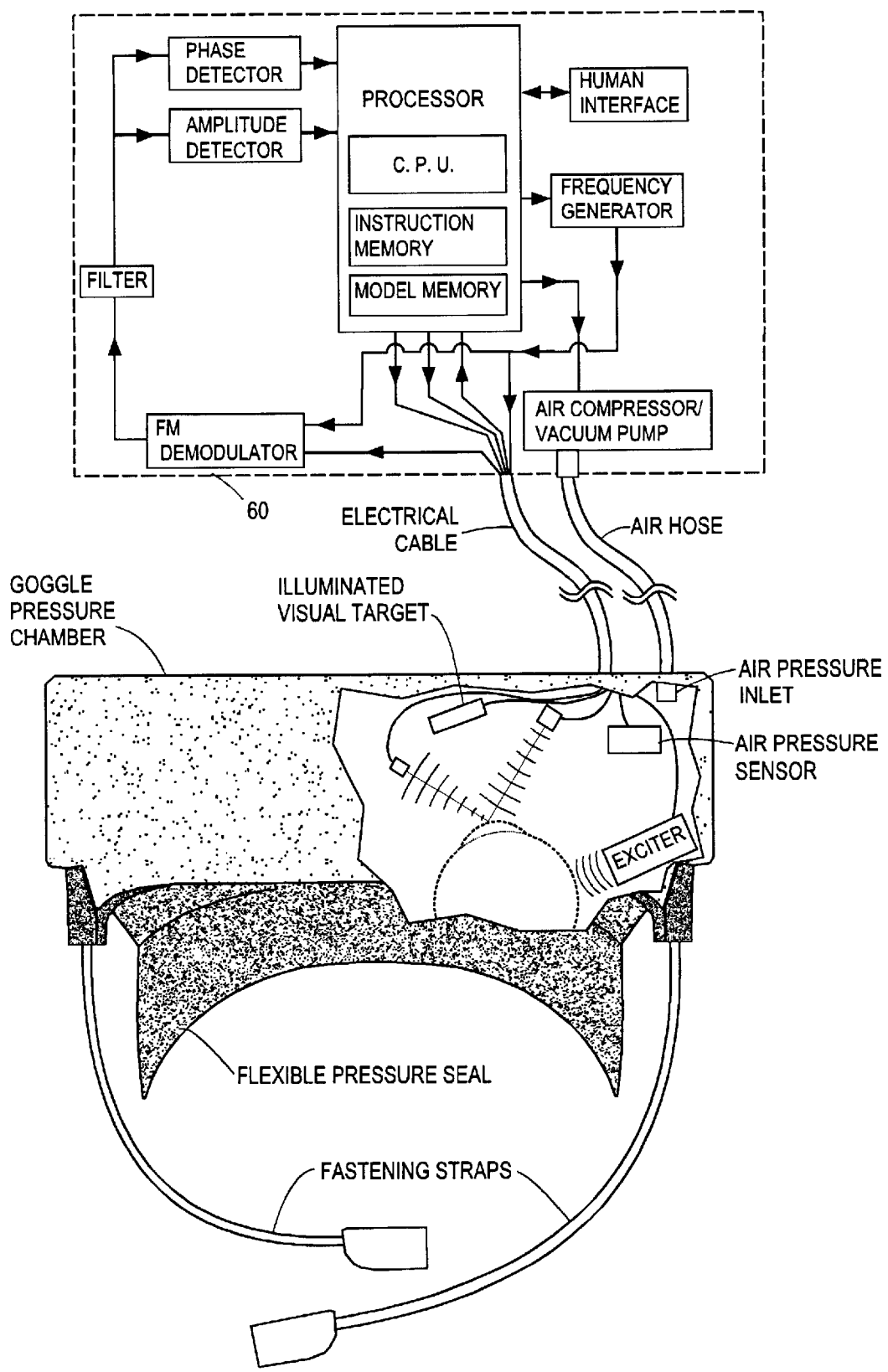
FIG._8

NONINVASIVE METHODS AND APPARATUSES FOR MEASURING THE INTRAOCULAR PRESSURE OF A MAMMAL EYE

FIELD OF THE INVENTION

The present invention relates to methods and apparatuses for measuring the intraocular pressure of an eye, and more particularly to tonometer methods and apparatuses for performing this measurement without touching the eye itself.

BACKGROUND OF THE INVENTION

Normal pressure within the human eye ranges between about 10 mm Hg and about 20 mm Hg above atmospheric pressure, which ranges between 700 mm Hg and 800 mm Hg at sea level, and which is nominally around 760 mm Hg at zero degrees Celsius. The eye pressure above atmospheric pressure is formally called intraocular pressure, or IOP. The intraocular pressure varies during the time of day by an amount of 3 mm Hg to 4 mm Hg, generally being highest in the morning. It also varies during the course of the year, generally being highest in the winter.

Glaucoma is a disease whereby peripheral vision is lost first, and it is related to elevation of the pressure within the eye to values higher than 21 mm Hg above atmospheric pressure. Such elevated pressure, over long duration, can cause blindness. Glaucoma affects as much as 2% to 3% of the population over the age of 40, and is a leading cause of blindness. The disease can be treated, but not cured, by application of one of a number of drug-therapy regimes. These regimes usually last for the rest of the patient's life, and require close monitoring and frequent eye-pressure measurements. In cases when the drug treatment is inadequate, laser or incisional surgery may be tried.

Instruments for measuring eye pressure are called tonometers. They are typically not portable, and could be quite expensive. Moreover, they need to be operated by a doctor or trained technician while the patient holds a fixed position with respect to the instrument. To date, there has not been a commercially successful tonometer which can be operated by the patient alone and that is portable and inexpensive, (although it should be mentioned that in April 2001 a new eyelid-contacting tonometer has been introduced, operating on the claimed experimental effect that when an object is pushed against the eye there will be a faint light halo appearing in the eye at the point in time when the external pressure at the area of contact equals the intraocular pressure at that moment.) The consequence of this is that frequent measurements of the patient's eyes are typically not made in order to determine the full range over which the patient's IOP varies. Because of this, doctors end up using a less than optimal application of the drug-therapy regimes since they do not have enough measurement data to fine-tune the regimes. In addition, a doctor may fail to suspect and diagnose a patient's glaucoma because the tonometer measurement may have been taken at a time when the patient's IOP was at its lowest point in the range during the measurement.

Most of the tonometers described above operate by pressing an area of the eye by a known force and then measuring the resulting displacement, or by pressing the area of the eye by a known displacement and measuring the force required to do so. The former approach may be conducted by an "air-puff" tonometer, which blows a puff of air toward the eye at a known force. Either of the above approaches may be conducted by a contact tonometer, which has a plunger that physically contacts the eye. Air-puff tonometers are uncomfortable, and contact tonometers require that the patient's eyes be anesthetized.

To address these problems, much research work has been done in the area of vibration tonometers. These tonometers apply vibrations to the eye, such as by a loud speaker or by a vibrating element contacted to the eyelid, vary the frequency of vibrations to find the maximum amplitude vibration of the eye (called the "resonance point"), and compute the IOP based on the frequency of maximum amplitude vibration. These tonometers are based on the assumption that the human eye can be modeled as a spherical body of water held together by the surface tension of the water (the so-called "water drop" model). Such a body of water has a plurality of vibratory modes n=1, 2, 3, . . . , each of which has a corresponding natural frequency, or resonant frequency $f_{n,res}$, at which the surface vibrations of the water drop are at maximums. The value of each resonant frequency depends upon the difference in pressure, $\Delta p$, between the interior of the water body and the external atmosphere, as provided by the following equation:

$$f_{n,res} = \lambda_n \cdot \frac{\sqrt{\Delta p / \rho}}{\pi \cdot a}$$

where:

$\lambda_n$ is the eigenvalue of the n-th mode, having approximate values of 1.0, 1.94, 3.0, and 4.18 for value of n=2 through n=5;

$\rho$ is the fluid density;

$\alpha$ is the radius of the sphere, and $\pi$ is a constant equal to the ratio of the circumference of a circle to its diameter (3.14159. . . ).

As applied to the eye, the pressure difference $\Delta p$ has been equated to the eye's intraocular pressure, as the IOP is defined as the pressure in the eye that is above atmospheric pressure. Many prior art approaches have used the above to model the eye.

However, it is important to note that the water-drop model predicts a zero value for each resonant frequency at 0 mm Hg of intraocular pressure. That is to say that at 0 mm Hg, $f_{1,res}=0$, $f_{2,res}=0$, $f_{3,res}=0$, $f_{4,res}=0$, etc.

As indicated by U.S. Pat. No. 5,865,742 to Massie (Non-Contact Tonometer), the use of this model for the measurement of intraocular pressure (IOP) has not met with success. The following quote from U.S. Pat. No. 5,865,742 points to some reasons for lack of success:

"One additional type is the vibration tonometer, first patented in the 1960's (U.S. Pat. Nos. 3,192,765 and 3,882, 718). In this device, it is proposed that the response of the eye to a vibrational excitation will be a measure of the IOP. The proposed exciters include very low-frequency sound and mechanical plungers. However, it is likely that the vibrational frequencies of the eye are affected by many factors not related to the IOP. It is, in fact, expected that the actual resonance spectrum of the eye would be dictated more by the connective tissue than by the IOP. All of these factors may be the reason why no commercial use of the vibration tonometer has been disclosed even though its development has been attempted" (Massey patent, column2, lines 50 to 62).

A thorough theoretical background going beyond the simple water balloon model is provided by "A Nonlinear Modal Frequency Response Analysis of the Pre-stressed Human Eye by the Finite Element Method" by K. C.

Henderson (submitted in partial fulfillment of the requirements for the degree Master of Science, University of Rochester, 1995) with experimental results described in a concurrent associated thesis for the same degree at the same university: "Intraocular Pressure Measurement Using Resonance Detection" by K. S. Bhella.

While vibration tonomoters offer the possibility of inexpensive and convenient measurement tools, they have not met with successful implementation, and consequently have not met with commercial success. The present invention is directed to providing a vibration tonometer that does not touch the surface of the eye and that provides accurate and reliable results, and which is affordable by home users.

SUMMARY OF THE INVENTION

In making their invention, the inventors have recognized that the "resonant frequencies" computed by the water-drop model do not account for the damping by the surrounding tissue and connective muscles, and that the frequencies computed by the model are, in reality, undamped natural frequencies that do not take into account the damping. The inventors have further determined that nearly all of the prior art vibration tonometers have measured each water-drop "resonant frequency" of the eye by finding a frequency at which an area of the eye's sclera undergoes maximum vibratory displacement when excited by an excitation source, and that this resonant frequency is below the natural frequency predicted by the water-drop model. The inventors have further found that the detection of the water-drop "resonant frequencies" is obscured due to the damping of the surrounding tissue and connective muscles.

In making their invention, the inventors have discovered that the sclera of the eye, which is the outer shell of the eye, has classes of undamped natural frequencies that are not predicted by the water-drop model, with each undamped natural frequency being associated with a corresponding vibratory mode of the shell formed by the eye's sclera and cornea. The value of each natural undamped frequency depends upon the intraocular pressure, increasing in value as this pressure increases. At each level of intraocular pressure, the natural frequencies in these classes are different in value from the damped and undamped natural frequencies of the water-drop model, and can be measured with less interference from the surrounding tissue and connective muscle. One characteristic of one of these classes of natural frequencies of the sclera is that their values approach a non-zero value when the intraocular pressure goes to zero mmHg. As another characteristic, when the curves of these frequencies versus intraocular pressure are extrapolated toward a value of zero frequency, the curves tend to converge to a common negative intraocular pressure value. These characteristics are different from the undamped natural frequencies of the water-drop model, all of which converge to a value of zero when the intraocular pressure reaches zero.

The inventors have further found that there is a band of vibratory frequencies around each undamped natural frequency which have similar properties as the corresponding undamped natural frequency, and which may be similarly utilized in the present invention. Each such band of vibratory frequencies includes the undamped natural frequency and the corresponding damped natural frequency, and is associated with the same vibratory modes associated with the undamped natural frequency. When a sinusoidal vibratory force with a frequency within such a frequency band is applied to a spot on the eye, such as by sonic pressure waves or ultra-sonic pressure waves, or is otherwise coupled to the eye, such as by a mechanical transducer contacted to tissue or bone near the eye, portions of the sclera and cornea surrounding or near the excitation spot vibrate in response with the same frequency. These portions are called "anti-nodes." Other portions of the sclera and cornea, called "nodes," remain relatively stationary while the anti-nodes vibrate. Each vibratory mode has a corresponding set of nodes and anti-nodes arranged in a corresponding pattern when the mode is excited. In general, an anti-node comprises a polygonal area covering a portion of the sclera and/or the cornea, and a node may comprise a great circle of a sphere, a small circle of a sphere, a line, or a point, all of which are located on the pseudo-spherical surface formed by the sclera and the eye. In general, the number of nodes and anti-nodes increases as the order of the mode increases. The band of vibratory frequencies associated with a corresponding vibratory mode is defined as the contiguous set of frequencies, which cause at least one node, and two anti-nodes of the mode's pattern to be present. For excitation frequencies that are between two separate but adjacent vibratory frequency bands, no regular pattern of nodes and anti-nodes is present.

Accordingly, the present invention encompasses methods and apparatuses for estimating the intraocular pressure of an eye, which is the difference between the pressure within the eye and the atmospheric pressure. Broadly stated, methods according to the present invention comprise measuring a first vibratory frequency of an associated vibratory mode of the sclera of the eye at an unknown intraocular pressure value, the first vibratory frequency having a value that varies as a first function of the eye's intraocular pressure. The first function has a form which extends or extrapolates to a non-zero frequency value for a zero value of intraocular pressure and to a zero frequency value for a negative value of intraocular pressure. Methods according to the present invention further comprise comparing the measured frequency value to one or more known values of the first vibratory frequency measured at corresponding known intraocular pressures to estimate value of the unknown intraocular pressure. Preferred embodiments of the present invention include measuring one or more additional vibratory frequencies of the cornea or the sclera of the eye at the unknown intraocular pressure value, and comparing their measured values to known values of the additional measured vibratory frequencies to estimate value of the unknown intraocular pressure. In preferred embodiments of the present invention, each of the vibratory frequencies comprises a corresponding undamped natural resonant frequency of the sclera or the cornea.

The present invention is in contrast to all prior art methods known to the inventors for estimating the intraocular pressure of the eye by vibratory excitation in that the present invention detects and measures vibratory frequencies that have non-zero values for a zero value of intraocular pressure.

The present invention is able to measure the vibratory frequencies of the eye's cornea or sclera more reliably and accurately than the prior art methods of measuring the "resonant frequencies" of the water drop model. The present invention is also able to do so without directly contacting the surface of the eye or shooting annoying puffs of air at the eye. Furthermore, the present invention is expected to be able to perform the measurements with relatively inexpensive components.

Accordingly, it is an object of the present invention to enable the measurement of the IOP of a patient's eye with an inexpensive and relatively portable tonometer.

It is another object of the present invention to provide a tonometer which can be operated by the patient at home or other places that are not at the doctor's clinic.

It is yet another object of the present invention to enable the patient's eye to be measured more frequently, and to thereby enable better health care.

These and other objects of the present invention will become apparent to those skilled in the art from the following detailed description of the invention, the accompanying drawings, and the appended claims.

BRIEF DESCRIPTION OF THE DRAWINGS

FIG. 1 is a graph of the square of the undamped resonant frequencies versus the intraocular pressure measured according to the present invention.

FIG. 2 is a schematic diagram of a mammal eye under vibratory excitation showing the measurement axes for the vibratory displacement of the excited portion of the eye, the velocity of said vibratory displacement, and the acceleration of said vibratory displacement, according to the present invention.

FIG. 3 is a set of graphs showing the vibratory displacement, velocity, and acceleration defined in FIG. 2, which are used to detect and measure the undamped natural frequencies according to the present invention.

FIG. 4 shows a first exemplary embodiment for exciting the eye with a forcing function and measuring the displacement of the eye at a location away from the excitation point according to the present invention.

FIG. 5 shows a second exemplary embodiment for exciting the eye with a forcing function and measuring the displacement of the eye at a location away from the excitation point according to the present invention.

FIG. 6 shows a third exemplary embodiment for exciting the eye with a forcing function and measuring the displacement of the eye at a location away from the excitation point according to the present invention.

FIG. 7 is a graph of the square of several undamped resonant frequencies versus the intraocular pressure to show several ways in which the measured frequency data at an unknown IOP pressure may be compared to measured frequency data at known IOP pressures to estimate the unknown IOP pressure according to the present invention.

FIG. 8 shows an exemplary apparatus for exciting the eye with a forcing function at various ambient pressure levels and measuring the displacement of the eye according to the present invention.

DETAILED DESCRIPTION OF THE INVENTION

The present invention is distinguished over the prior art vibratory methods in that it detects and measures the vibratory frequencies of the sclera and the cornea, the shell membranes which enclose the eye, rather than the resonant frequencies arising from the water and gel mass within eye. We have observed from theoretic analysis that there are two classes of vibratory modes of the composite shell membrane formed by the sclera and the cornea. Both classes of vibratory modes exhibit motions of the sclera and cornea that move tangentially to the surface of the sclera and cornea (i.e., in-plane motions), and motions that move transverse to the surface of the sclera and cornea (i.e., radial motions). In one class, the tangential motions dominate over the transverse motions; in the other, the transverse motions dominate over the tangential motions. Each class of vibratory modes has a set of vibratory frequency bands, with each band corresponding to a vibratory mode of the class. In turn, each vibratory frequency band comprises an upper frequency, a lower frequency, and a continuum of frequencies therebetween, with each such band containing both the damped and undamped natural frequencies of the band's corresponding vibratory mode. As described below in greater detail, when a vibrating force having a frequency within one of the vibratory bands is applied to the sclera or the cornea, a pattern of vibrating portions (called "antinodes") and stationary portions (called "node") is established over the surface of the sclera.

A defining characteristic, or "signature," of a vibratory mode is its undamped natural frequency. This is the frequency at which the vibrating portions would undergo their maximum vibratory displacements if there were no damping elements coupled or connected to the sclera or the cornea. FIG. 1 shows a plot of the squares of four measured frequency values of the exemplary undamped natural frequencies for three corresponding vibratory modes of the cornea of a pig's eye plotted as a function of the intraocular pressure. Measured data for pressures between 20 and 50 cm water are plotted with solid curves. Values for pressure values below 20 cm water are extrapolated and shown by dashed curves. Initially bovine and then pig and rabbit eyes have been used to develop and demonstrate the present invention since all have enabled us to conduct outside-of-the-body measurements over a wide range of intraocular pressure values. However, the size of a pig's eye is close to that of a human eye. The value of each undamped natural frequency varies as a respective function of the eye's intraocular pressure. When the frequency squared is plotted as a function of the pressure, these functions have graphs that are substantially equal to a set of spaced-apart straight lines, one straight line per undamped natural frequency, with each such line having a positive slope and a non-zero frequency value at zero pressure (i.e., a non-zero frequency intercept on the chart shown in the Figure). The straight lines can be extrapolated into the quadrant of negative pressure, where they tend to converge to a common negative pressure value near or at a frequency value of zero Hertz. In any event, each extrapolated line passes through a negative pressure value for a value of zero Hertz for the corresponding undamped natural frequency.

A plotting of the upper and lower frequencies of each vibratory frequency band would exhibit similar characteristics. Specifically, the lower frequency of each band would follow a generally straight line that would have a non-zero value at zero pressure, as would the upper frequency of each band. In addition, we currently expect that a number of other vibratory frequencies within the vibratory band will exhibit similar characteristics.

We have observed that the value of an undamped natural frequency also depends to a lesser extent upon the location of the measurement point on the eye. For example, we have observed that a measurement of an undamped natural frequency made at the center of the cornea is different from a measurement made away (e.g., 2 mm away) from the center of the cornea or elsewhere at the side of the eye (on the sclera), although the intraocular pressure is the same for both measurements. We believe that this variation is due to the differences in the composition, thicknesses, and radii of curvature at different locations of the cornea and sclera. The other vibratory frequencies in band are expected to have similar spatial variations. Nonetheless, the vibratory frequencies are still useful in estimating IOP values, particularly when the measurements are always made at a set location on the eye (e.g., the cornea).

An analytical study of the eye's sclera and cornea has been preformed based on the model of a spherical shell, to find that the functions of the undamped natural frequencies of a segment (i.e., portion) of the cornea or sclera have the following theoretical form:

$$(unf_n)^2 = (unf_{n,0})^2 \cdot \left[1 + \frac{r_0 \cdot (1-v)}{T \cdot E} \cdot \Delta p\right] \quad [1]$$

where:

$unf_n$ is the undamped natural frequency of the n-th vibratory mode as measured at the segment for the given value of intraocular pressure value $\Delta p$;

$unf_{n,0}$ is the undamped natural frequency of the n-th vibratory mode as measured at the segment for a zero value of intraocular pressure ($\Delta p=0$);

$r_0$ is the average radius of curvature of the segment;

$v$ is the average Poisson's ratio of the material (e.g., sclera or the cornea) at the location of the segment (the Poisson's ratio is the ratio of the induced transverse strains to the axial strain);

T is the average thickness of the material (e.g., the sclera or cornea) at the location of the segment; and E is the average Young's modulus of material (e.g., the sclera or cornea) at the location of the segment. The Young's modulus is also called the modulus of elasticity, and is the ratio of a stress applied to a material to the resultant strain of that material.

By setting $\Delta p=0$ in equation [1], it can be seen that the theoretical model predicts that each undamped natural frequency $unf_n$, as measured at a particular segment, has a non-zero value $unf_{n,0}$ at zero intraocular pressure $\Delta p=0$, as is seen by the extrapolated lines of FIG. 1. This is true regardless of how the frequencies are plotted. The model further predicts that the square of each natural frequency $(unf_n)^2$, as measured at a particular segment, increases as a linear function (i.e., straight line function) of the intraocular pressure $\Delta p$. In addition, by setting $unf_n=0$ in equation [1], the theoretical model predicts that the functional forms of the undamped natural frequencies converge to a common negative pressure point $P_C$ when the functional forms are extrapolated into the negative pressure quadrant. The negative pressure point $P_C$ is given by equation [2]:

$$\text{Negative pressure point } P_C = -\frac{T \cdot E}{r_0 \cdot (1-v)} \quad [2]$$

The extrapolated lines shown in FIG. 1 essentially converge at a negative pressure point, which we have indicated as point $P_C$. The values of $r_0$, $v$, T, and E generally remain relatively constant over a period of several months, and usually change only gradually if they change at all.

In preferred method embodiments of the present invention an undamped natural frequency of an associated vibratory mode of a segment of the sclera or cornea is measured at an unknown intraocular pressure value, and then compared to one or more known values of the same undamped natural frequency previously measured at corresponding known intraocular pressures (and preferably at the same segment) to estimate value of the unknown pressure. One manner of performing the comparison is to fit the known frequency squared values as a linear function of the known pressure values, such as one of the lines shown in FIG. 1. The measured frequency is then compared with the fitted line to estimate a value for the unknown pressure.

We now compare the vibratory frequencies of the present invention with those of the prior art water-drop model. As can be seen from FIG. 1, the undamped natural frequencies of the sclera and the cornea have positive, non-zero, values for an intraocular pressure value of zero, in contrast to the resonant frequencies of the water drop model, which have zero values for zero intraocular pressure. As another difference, the curves of the natural frequencies of the sclera and the cornea extrapolate to a negative pressure for zero frequency values, generally to a single negative pressure point $P_C$, whereas the curves of the water-drop model go to zero pressure as the frequencies go to zero Hertz. As yet a further difference, the vibratory frequencies are different from each other by at least 50 Hz for pressures.

Measurement of the Vibratory Frequencies of a Vibratory Mode

FIG. 2 shows an approximate cross-sectional depiction of a mammal eye under vibratory excitation by a force F(t) at an area of the eye identified as the excitation point. As examples, force F(t) may be provided by sonic pressure waves (e.g., below 20 kHz), ultra-sonic pressure waves (e.g., between 20 kHz and 1 MHz) modulated by a lower frequency signal, or by mechanical transducer contacted to the orbital bone, the globe or tissue near the eye. In preferred embodiments, Force F(t) has a sinusoidal form, with a frequency value that can be varied. A dashed circle 36 shows the eye at rest before the excitation. As force F(t) oscillates, the displacement x at the excitation point vibrates in response. The directional definition for the displacement x is shown by axis 31, along with axes 32 and 33, which show the directional definitions for the velocity v and acceleration α, respectively, of the excitation point. When force F(t) oscillates at a frequency within the band of vibratory frequencies of a vibratory mode, such as at the undamped natural frequencies within such a band, the eye has several areas that vibrate in response to the force and with the same frequency. These areas are called anti-nodes, and each anti-node comprises a polygonal area which covers the sclera or the cornea. The eye also has several areas that do not vibrate, which are called nodes. In general, a node may comprise a great circle of a sphere, a small circle of a sphere, a line, or a point, all of which are located on the surface of the sclera or the cornea. (Each node is indicated by a dot in the Figure because the figure is a cross-sectional view.) The solid line 37 shows a "snap-shot" of the eye's cross-section under excitation at the vibratory frequency, and taken at a time when the anti-nodes are near their maximum displacement (the amount of displacement has been exaggerated for the sake of clarity). The locations of the nodes fall on the dashed circle 36 (the eye at rest), and the anti-nodes areas appear between the nodes. Each anti-node vibrates between an inward position, which has less curvature than the area has during rest, and an outward position, which has more curvature than the area has during rest. A similar scenario occurs on the cornea itself as it is composed of a continuum of rings of spheres with varying diameters.

Each vibratory mode has a corresponding pattern of nodes and anti-nodes distributed over the shell surface formed by the eye's sclera and cornea when the mode is excited, and there is a band of vibratory frequencies that will cause the mode's pattern to appear. The band of vibratory frequencies associated with a corresponding vibratory mode is defined as the contiguous set of frequencies which cause at least one node and at least two anti-nodes of the mode's pattern to be present, the first node being adjacent to the first anti-node, and the second anti-node being adjacent to the first node. For excitation frequencies that are between two separate but adjacent vibratory frequency bands, no clear pattern of nodes and anti-nodes is present. As indicated above, each band of vibratory frequencies includes an undamped natural frequency and the corresponding damped natural frequency. An estimate of the upper and lower useful bounds for a band of vibratory frequencies provided in terms of phase and amplitude measurements is given below.

For the particular mode described in FIG. 2, when force F(t) is at a vibratory frequency, the displacement of each anti-node is either substantially in phase or substantially 180-degrees ($\pi$ radians) out of phase with the displacement x at the excitation point (provided, of course, that the displacements are measured with the directional convention of axis 31, where axis 31 is moved to the nodal area and placed in a similar orientation as it is placed at the excitation point). For example, one anti-node in FIG. 3 is identified as "Measurement Point" with corresponding axes 31'–33', and its displacement x' is substantially 180-degrees out of phase with the displacement x of the excitation point. Its velocity v' and acceleration $\alpha$' are similarly substantially 180-degrees out of phase with those of the excitation point. We say that each anti-node is either "substantially" in phase or "substantially" 180-degrees out of phase with the displacement x at the excitation point, rather than saying "exactly" in phase or "exactly" 180-degrees out of phase, because the aforementioned differences in composition, thickness, and curvature radius in the various segments of the sclera and cornea will cause some spatial variations in phase, just as the aforementioned differences cause spatial variations in the values of the natural frequencies at the anti-nodes.

FIG. 3 is a set of graphs 41–43 showing the vibratory displacement x(t), velocity v(t), and acceleration $\alpha$(t), respectively for the excitation point under the above-described excitation of force F(t), with the directional convention shown by axes 31–33 of FIG. 2. The displacement x(t) of the excitation point is shown at 44 in graph 41, and the displacement x'(t) measured at the "Measurement Point #1" is shown by the dashed line 45. The latter curve is substantially 180 degrees out of phase with respect to the first. From the laws of physics, the velocity v(t) is a sinusoidal curve which leads the sinusoidal curve of the displacement x(t) by 90-degrees($\pi$/2 radians), and the acceleration $\alpha$(t) is a sinusoidal curve which leads the sinusoidal curve of the velocity by 90-degrees. Stated in another way, the displacement sinusoid x(t) lags the velocity sinusoid v(t) by 90-degrees, and lags the acceleration sinusoid $\alpha$(t) by 180-degrees.

We now examine the case for a family of vibrational modes where the frequency of excitation force F(t) is varied from a starting value which is below an exemplary undamped natural frequency $unf_k$ (n=k) of the k-th vibratory mode, and also below the corresponding vibratory frequency band of that mode, to an ending point which is above $unf_k$ and the corresponding vibratory frequency band. At the starting frequency, the displacement sinusoid x(t) substantially at the excitation point coincides with the force sinusoid F(t), and the phase difference between the two sinusoids is near zero degrees. At this point, the k-th vibratory mode is not excited, the excitation point of the eye passively follows the forcing function F(t), and the modes pattern of nodes and anti-nodes is not established. As the frequency of F(t) increases, the displacement sinusoid x(t) begins to lead or lag the force sinusoid F(t), the k-th vibratory mode begins to be excited with the mode's pattern of nodes and anti-nodes being formed over the shell comprised by the eye's sclera and cornea. This frequency value defines the lower bound of the vibratory frequency band. An anti-node develops at the excitation point, energy is transferred to the anti-nodes adjacent to the excitation point, and the anti-nodes begin to vibrate with the frequency of F(t). The frequency of F(t) then increases to the point where the excitation point reaches a maximum amplitude in its displacement. The frequency at which this occurs is the damped natural frequency of the mode for the excitation point. (Because of the variation in the composition, thickness, and radius of the sclera and cornea, the other anti-nodes usually experience maximum amplitudes in their displacements at somewhat different frequencies.) Because of damping, the phase difference between and F(t) at this point is less than +90 degrees (but above zero degrees) when x(t) leads F(t), or is less than −90 degrees (but below zero degrees) when x(t) lags F(t). The two possible situations are the result of the nature of the analytical expression of the vibrational movement. We note that a lag of 270 degrees is the same as being ahead by +90 degrees. We define the phase difference between x(t) and F(t) at this point (where the anti-node reaches maximum amplitude in its displacement) as $\theta_{MA,k}$. Instances of the quantity $\theta_{MA,k}$ may be defined for other anti-nodes (particularly for a measurement point which is not the same as the excitation point), and those instances may have somewhat different values than that for the excitation point.

As the frequency of F(t) is increased, the amplitude of the excitation point decreases. At some point above the damped natural frequency, the phase difference between x(t) and F(t) reaches +90 degrees or −90 degrees, as the case may be. At this point, the frequency equals the value of the k-th undamped natural frequency $unf_k$, as measured at the excitation point, and the forcing sinusoid F(t) is in phase or 180 degrees out of phase with the velocity sinusoid v(t). If no damping were present in the system, the excitation point would undergo its maximum amplitude at frequency $unf_k$. (Because of the variation in the composition, thickness, and radius of the sclera and cornea, the other anti-nodes usually experience a ±90 phase difference between their displacement and F(t) at somewhat different frequencies, and thus have somewhat different natural frequency values.)

We define the difference in phase between the undamped natural frequency and the damped natural frequency (corresponding to the point of maximum amplitude) at any given anti-node as: $\theta_{D,k}=90°-\theta_{MA,k}$ in the case where x(t) leads F(t), or $\theta'_{D,k}=-90°-\theta_{MA,k}$ in the case where x(t) lags F(t). At a frequency above the point where the phase difference is between +90 degrees and +180 degrees or −90 degrees and −180 degrees at the excitation point, the k-th mode's pattern of nodes and anti-nodes disappears, which defines the upper bound of the vibratory frequency band. With further increases in the frequency of F(t) beyond $unf_k$, the phase difference between sinusoids x(t) and F(t) at the excitation point reaches in many cases +180 degrees (or −180 degrees, which is from a practical stand point the same as +180 degrees), at which point the forcing sinusoid F(t) is in phase with the acceleration sinusoid $\alpha$(t).

From the above, the damped natural frequency of a vibratory mode measured at a selected anti-node can be found by finding a maximum in the displacement of the selected anti-node within the band of vibratory frequencies associated with the vibratory mode. The undamped natural frequency of a vibratory mode measured at a selected anti-node may be detected and measured in the present invention by finding the frequency within the band of vibratory frequencies at which the phase difference between the displacement sinusoid and F(t) is +90 or −90 degrees. During a typical measurement session, a force emitter is directed to the excitation point on the eye to provide the forcing function F(t), and a displacement detector is located at another point of the eye to measure the phase and amplitude of an anti-node. The frequency of F(t) is then swept through a range of frequencies that includes several undamped natural frequencies. While we have shown in FIG. 2 that the excitation force F(t) is directed to a certain point, it may be directed at other locations on the eye, such as to the side, top or bottom of the eye. In addition, while we have shown a measurement point at the cornea, it may be at the side of the eye.

The value of the undamped natural frequency and the number of anti-nodes increases with the value of the mode index n. Given that the surface area of the sclera/cornea shell is nearly constant, this means that the surface area of each anti-node and the spacing between the centers of adjacent anti-nodes decrease as the value of the mode index n increases, and as the value of the undamped natural frequency increases.

This factor should be taken into account when detecting and measuring the undamped natural frequencies. As a simplistic approach, one can look for phase differences, as measured by a phase detector, which are within a few degrees of +90 or −90 degrees as the frequency is swept through a range of frequencies that is broad enough to include several undamped natural frequencies. As another approach, the frequency of the forcing function is swept as before, and the pending encounter of an undamped resonant frequency is detected by detecting a peak in the amplitude of the measured displacement. At peak amplitude, the phase difference between the forcing function F(t) and the measured displacement will be within approximately $|\theta_{D,k}|$ of either +90° or −90°, with $|\theta_{D,k}|$ being less than 90° in value. The frequency is then increased further through the point where the phase difference is precisely +90 or −90 degrees. The sweeping to further increased frequencies can continue in the same fashion through several resonances.

From our experimental work to date, we believe that the measurement accuracy of the vibratory frequencies can be increased by certain selections of the excitation point, the measurement point, and the orientation of the displacement detector with respect to the excitation force. In resonance, the sclera and cornea have tangential motions and radial motions, as well as a translatory motion along the direction of the excitation force. The translatory motion moves the entire eye as a unit, and is not reflective of the motions of the vibratory modes that we are interested in, i.e., the tangential and radial motions. Thus, we feel that it is important that the detector be arranged to increase the detection of the tangential and radial motions (since they are reflective of the vibratory frequencies that we are interested in), and decrease the detection of the translatory motion. This may, for example, be accomplished by measuring the vibratory displacement at the center of the cornea while the exciting force operates at a point where the direction of the force is substantially perpendicular to the induced movement of the cornea (such an excitation point could be on the eyelid at the temporal corner of the eye, toward the ear). In addition, from our work, we currently believe that it is beneficial to position the detector at such angle that it will be measuring the motion of the cornea in the direction that is as close as possible to being perpendicular to the direction of the exciting force. We currently believe that the angle formed from the measurement point to the center of the eye and to the excitation point should be within 30 degrees of a 90-degree angle, and more preferably within 20 degrees thereof, and most preferably within 10 degrees thereof.

While we currently believe that the above arrangements are preferable for obtaining good measurements, we do not preclude the possibility that further investigation will find other beneficial arrangements in the future.

In addition, we currently believe from our experimental results that the consistency in the measurements made at different times of the day and month can be improved by measuring at the same point on the eye. However, we do not preclude the possibility that further investigations will find ways in which the same or better consistency can be achieved without measuring at the same point on the eye.

Use of Other Vibratory Frequencies

While preferred embodiments of the present invention use measurements of one or more undamped natural frequencies to estimate the unknown intraocular pressure, the damped natural frequency may be used as well. In this case, a damped natural frequency for a vibratory mode is measured and then compared to values of the same damped natural frequency previously measured at known intraocular pressures. Furthermore, other vibratory frequencies within the corresponding vibratory frequency band may be used. In this case, a particular vibratory frequency in a band may be uniquely identified from measurement to measurement by the corresponding phase difference between F(t) and the displacement sinusoid that exists at the frequency, by the corresponding percentage of amplitude relative to the peak amplitude that exists at the frequency.

As described above, the upper and lower bounds of each vibratory frequency band were defined in terms of the establishment of the mode's anti-nodes and nodes. From a practical matter, one generally selects a vibratory frequency within the band of frequencies that have corresponding anti-node amplitudes at the measurement point that are between 25% and 100% of the maximum amplitude achieved in the band at the measurement point (i.e., amplitudes within 12 dB of the peak amplitude). Selection within the band may also be done on the basis of the phase difference between F(t) and x(t). For example, in preferred embodiments, a vibratory frequency for the k-th mode may be selected such that this phase difference is in the range of $(\theta_{MA,k}-\theta_{D,k})$ to $(90°+\theta_{D,k})$ in the case where x(t) leads F(t), and in the range of $(-90°+\theta'_{D,k})$ to $(\theta_{MA,k}-\theta'_{D,k})$ in the case where x(t) lags F(t). This range covers the frequencies that are within $\theta_{D,k}$ of either of the damped and undamped natural frequencies of the band (as measured at the measurement point), as well as the frequencies between the two natural frequencies.

From the above, we may generalize equation [1] as follows:

$$(f_n)^2 = (f_{n,0})^2 \cdot \left[1 + \frac{r_0 \cdot (1-v)}{T \cdot E} \cdot \Delta p\right] \quad [3]$$

where:

$f_n$ is the value of a selected vibratory frequency in the vibratory frequency band of the n-th vibratory mode for the given value of intraocular pressure value $\Delta p$ and as measured at a selected segment (i.e., portion) of the cornea or sclera (e.g., as measured at an anti-node); and $f_{n,0}$ is the value of the selected vibratory frequency $f_n$ at a zero value of intraocular pressure ($\Delta p = 0$), as measured at the selected segment.

Excitation and Detection Apparatuses

FIG. 4 shows an example where the excitation may be provided acoustically, and the detection may be accomplished optically by directing a light beam on the excitation point and measuring changes in the reflected light. FIG. 4 follows the approach used in U.S. Pat. No. 3,882,718 to Kriebel, but is different in that the excitation point and the measurement point are different. A housing 60 contains both the exciter (in this case a pressure wave emitter) and the displacement detector. The exciter may comprise a pair of oppositely disposed loudspeakers which are attached to a closed chamber, and a tube which directs the sound from the chamber out to the eye in the form of pressure waves. A common sinusoidal voltage source is applied to the loud speakers to drive them in phase. On a positive half-cycle of voltage, the diaphragms of the loud speakers move toward one another to increase the pressure within the chamber. On a negative half-cycle, the diaphragms move away from one another to create a negative pressure in the chamber. The pressure changes in the chamber are coupled to the eye by the pressure waves, to provide forcing function F(t) to the excitation point of the eye. The displacement detector comprises two light tubes 61 and 62 that are directed toward the cornea of the eye, as shown in the Figure, a light source 70 disposed at the distal end of light tube 61, and a lens 68 that focuses the light beam from source 70 onto the excitation point (e.g., cornea) of the eye. Light tube 62 is positioned to receive the reflected light from the excitation point. A lens 74 within the tube focuses the reflected light onto a spatial photodetector 78. As the eye is excited by the acoustic pressure from the loud speakers, the surface of the excitation point vibrates and changes the angle of the reflected light. As a result, the position of the light spot focused onto detector 78 oscillates, as indicated by the double-arrow line near detector 78. The oscillation of the spot's position is converted into a corresponding oscillating electrical signal. In this example, the measurement point for the displacement x'(t) is not the same as the excitation point, and thus there is a half-cycle phase ambiguity between the displacement x'(t) and the excitation force F(t) which must be considered. An illuminated target is preferable and included to direct the patient to hold the eye steady in a substantially fixed position.

The sinusoidal signal for the speakers of the exciter is provided by a variable frequency generator, which in turn is controlled by a data processor. The data processor controls the frequency generator so as to sweep the exciter (e.g., pressure wave emitter) through a range of frequencies for F(t) which includes one or more vibratory resonant frequencies, which are preferably undamped natural frequencies. During the sweep of the excitation frequency, the output signal of photodetector 78 is provided to a phase detector and an amplitude detector, each of which may be of conventional design. The output of the photodetector is preferably processed by a filter to reduce low-frequency components (which may be caused by movement of the patient) before being provided to the inputs of the amplitude and phase detectors. The phase detector receives a signal from the frequency generator, and both it and the amplitude detector provide outputs to the processor. The processor comprises a central processing unit (CPU) which is capable of reading the outputs of the detectors and issuing instructions to the frequency generator, a memory (i.e., computer-readable medium) for holding sets of instructions which direct the CPU to perform several sequences of operations, and a memory (i.e., computer-readable medium) for holding the model parameters of the patient's eyes. The instruction sets and the model parameters are described below in greater detail.

FIG. 5 shows an example of where the optically-based displacement detector has been replaced by an ultrasonic-based detector. Here, an ultrasonic emitter emits pressure waves in the frequency range above 20 kHz (typically between 20 kHz and 10 MHz) toward the cornea of the eye. A portion of the waves bounce off of the cornea and propagates toward an ultrasonic detector. One exemplary implementation of detection is as follows. The signal received by the detector follows the frequency of the signal emitted by the ultrasonic emitter, but is amplitude modulated (AM) and frequency modulated (FM) by the vibration of the measurement location on the eye (e.g., cornea). In general, the FM modulation signal is more useful, with a rise in frequency corresponding to an outward displacement of the cornea, and a fall in frequency corresponding to an inward contraction of the cornea. After accounting for the phase delays caused by the spacing between the eye and the force wave emitter and the spacing between the cornea and the ultrasonic detector, the phase of the demodulated FM signal can be compared against the phase of the emitted pressure waves of the force wave emitter to locate the undamped natural frequencies, and the amplitude of the demodulated FM signal may be analyzed to find a maximum value within a resonant frequency band to locate the damped natural frequency. Since the patient may move during the measurement process, and since such unintended movements are picked up in the demodulated FM signal, the demodulated FM signal is preferably low pass filtered (e.g., 100 Hz and below) to remove the disturbance of such movements.

As in the embodiment of FIG. 4, the CPU, frequency generator, and phase detector are used in the embodiment of FIG. 5 in the previously-described manner. The signal from the ultrasonic detector is provided to the input of an FM demodulator, which generates an output signal to produce a signal which is representative of the displacement of the cornea. Such detectors are well known in the art. To improve the FM demodulation accuracy, the phase detector may also receive a signal from the ultrasonic emitter which is representative of the output frequency of the ultrasonic emitter. The output of the demodulator is preferably processed by a filter to reduce low-frequency components, and then provided to the inputs of the amplitude and phase detectors.

FIG. 6 shows an example of where the ultrasonic-based detector of FIG. 5 has been replaced by an optical interferometer which measures the displacement of the cornea. The interferometer creates an interference pattern from light bounced off the cornea of the eye, and determined the displacement by observing the changes in the interference rings of the interference pattern. The CPU, frequency generator, phase detector, amplitude detector, and filter are used in this embodiment as they are in the embodiment shown in FIG. 4.

While each of the embodiments above have used a vibratory exciter which comprises a pressure wave emitter, it may be appreciated that other species of vibratory exciters may be used, such as mechanical vibrators (driven by a piezoelectric, electromagnetic or other transducers) which have output pads that touch a cheek bone or tissue near the eye (such as an the eyelid on its outer side while the eyelid is open), or a vibratory mouth piece. It may be further appreciated that the photo-detector 78 shown in FIG. 4, the ultrasonic detector and FM demodulator of FIG. 5, and the interferometer of FIG. 6 are each exemplary embodiments of a displacement detector which detects vibratory displacements of a surface area of the eye and provides an electrical output signal that is representative of the vibratory displacements.

In exemplary embodiments of the present invention, the processor shown in FIGS. 4–6 has a set of instructions (called the "excitation instruction set") stored in the instruction memory that directs the processor to command the controlled frequency generator to output a plurality of waveforms at a plurality of different frequencies, and a another set of instructions (called the "monitor instruction set") that directs the processor to monitor the output of the phase detector and/or amplitude to detect one or more vibratory frequencies, which are called herein "the measured vibratory frequencies." The values of the measured vibratory frequencies, of course, depends upon the intraocular pressure (IOP) of the eye at the time of the measurement. In preferred implementations, the excitation instruction set directs the frequency generator to sweep its output frequency over a range beginning at approximately 100 Hz up to approximately 2000 Hz, either in the ascending direction or the descending direction. (Sweeping between 100 Hz and 4000 Hz is also possible). Also in preferred implementations, the monitor instruction set directs the processor to monitor the output of the phase detector and/or the output of amplitude detector for the characteristic signal patterns of the vibratory frequencies that the tonometer is programmed to measure. As each characteristic signal pattern is encountered, the frequency of the frequency generator is obtained and identified as a measured vibratory frequency. In some implementations, the processor actively steps the frequency generator by increments, with the current frequency value being stored in a register. The vibratory resonant frequency may be obtained from this register when the characteristic pattern is detected. In other implementations, the processor may allow the frequency generator to increment its frequencies itself, in which case the processor issues a request to the frequency generator for its current output frequency value when the processor detects a characteristic pattern of a vibratory frequency from the detector signals. When using damped natural frequencies of the vibratory modes as the vibratory frequencies, the characteristic patterns comprise peaks in the signal of the amplitude detector. When using the undamped natural frequencies, the characteristics comprise the appearances of a clear +90 or −90 degree phase shifts between the forcing sinusoid F(t) output by the exciter and the measured sinusoidal displacement of the eye's outer surface. The confidence level in the detection of each undamped natural frequency can be increased by ensuring that there is a nearby peak in the signal of the amplitude detector. In this case, the characteristic pattern may be the occurrence of an amplitude peak followed shortly thereafter by the occurrence of a ±90 phase shift when the frequency is swept in the increasing direction, or the characteristic pattern may be the occurrence of a ±90 phase shift followed shortly thereafter by the occurrence of an amplitude peak when the frequency is swept in the decreasing direction. If one wishes to use other vibratory frequencies besides the undamped and damped natural frequencies, the detection of specific phase shifts (other than ±90 degrees) may be used as characteristic patterns.

Generation of an Estimate of an Unknown IOP

In exemplary embodiments of the present invention, the processor shown in FIGS. 4–6 has yet another set of instructions (called the "estimation instruction set") stored in the instruction memory that directs the processor to compute an estimated pressure from a set of measured vibratory frequencies and a model of the eye being tested. We provide a number of examples of how the estimate can be generated, along with corresponding exemplary forms of the estimation instruction set.

Single Vibratory Frequency Embodiments

There are a number of approaches for applying the model of Equations [1] and [2]. Referring to FIG. 1, it can be seen that over the pressure range of interest, generally 6 mmHg to 32 mmHg (corresponding to 8 $cmH_2O$ to 42 $cmH_2O$), the undamped natural frequency of the lower-order vibratory mode 1 can be clearly distinguished from the undamped natural frequencies of the higher-order vibratory modes 2 and 3. In the figure, we have enclosed this area with a rectangular box 5. Thus, one can have reasonable certainty that the undamped natural frequencies measured in the frequency range of about 100 Hz to about 400 Hz (corresponding to squared frequencies of $0.01 \times 10^6$ $Hz^2$ to $0.16 \times 10^6$ $Hz^2$) over the pressure range of 6 mmHg to 32 mmHg at various times for an eye are associated with the same vibratory mode, i.e., the lower vibratory mode 1. The other vibratory frequencies within the band of vibratory frequencies for the lower mode 1 are confined to a slightly larger frequency span, but are still distinguishable from the bands of vibratory frequencies of the higher-order vibratory modes 2 and 3. As for the next higher vibratory mode 2, its undamped natural frequency can be clearly distinguished from those of vibratory modes 1 and 3 in the IOP pressure range of approximately 3 mmHg to approximately 11 mmHg, spanning the squared frequency range of about $0.16 \times 10^6$ $Hz^2$ to about $0.47 \times 10^6$ $Hz^2$ (corresponding to the frequency range of approximately 400 Hz to approximately 690 Hz).

Accordingly, the following exemplary approaches of applying the model of Equations [1] and [2] may be employed. One or more measurements of a vibratory frequency associated with this lower vibratory mode 1 are made at different but known values of IOP pressure. A conventional tonometer is used to measure the IOP values and a tonometer according to the invention is used to obtain the measured frequency values of the vibratory frequency. One may then measure a frequency value of the vibratory frequency at an unknown IOP pressure with a tonometer according to the present invention and then compare that measured frequency value to the one or more frequency values that were previously measured at known IOP pressures. In a rudimentary embodiment, one known frequency value at one known IOP pressure is used, preferably one having an IOP pressure in the range of 16 mmHg to 20 mmHg. The vibratory frequency value measured at the unknown IOP pressure may be compared against the vibratory frequency value measured at the known IOP pressure, and then the pressure may be estimated as either being above or below the known IOP value. The rudimentary embodiment may serve the purpose of letting the patient know if his/her eye is within an acceptable range (e.g., below 18 mmHg) or in an unacceptable range (e.g., above 18 mmHg). Specifically, if the measured frequency at the unknown IOP pressure is below the measured frequency made at a known IOP pressure of 18 mmHg, as an example, then the rudimentary embodiment provides an indication that patient's eye is within an acceptable range. If it is above, then the rudimentary embodiment provides an indication that patient's eye is not within an acceptable range.

If the exemplary apparatus measures an undamped natural frequency that is above approximately 400 Hz, then, without having further information, there is an ambiguity as to whether the measured frequency belongs to the lower vibratory mode 1 (in which case the corresponding IOP would be approximately 32 mmHg) or to the next higher vibratory mode 2 (in which case the corresponding IOP would be approximately 6 mmHg). In this instance, the exemplary tonometer according to the present invention can output the following message to the patient: "PRESSURE OUT OF RANGE—SEE DOCTOR".

This rudimentary approach may be implemented in the tonometers shown in FIGS. 4–6 by storing the known IOP pressure value and its corresponding value of the vibratory frequency of vibratory mode 1 in the "model memory" of the processor, and by having the estimation instruction set (stored in the instruction memory of the processor) direct the processor to undertake the above comparison step to generate an estimated pressure ("acceptable" or "unacceptable") after the processor obtains the measured vibratory frequency at the unknown IOP pressure under the direction of the excitation instruction set and the monitor instruction set.

An improved rudimentary embodiment builds on the previous approach, and adds a slope extrapolation feature. From studies on pig eyes, we anticipated that the undamped natural frequency of the lower vibratory mode 1 will change at a rate of approximately 10 Hz per 1 mmHg change in IOP in the nominal IOP range for the general human population. One can then make one frequency measurement at a known IOP pressure in the range of 15 mmHg to 20 mmHg, and then compare the measured frequency value made at an unknown IOP against the frequency measured at a known IOP value, and thereafter extrapolate according to an exemplary slope of 10 Hz per 1 mmHg. For example, if the frequency measurement at the unknown IOP pressure is 20 Hz above the frequency value measured at the known IOP pressure, then a value of (20 Hz)*(1 mmHg/10 Hz)=2 mmHg is added to the known IOP pressure to generate the estimate of the unknown IOP pressure. If the frequency measurement at the unknown IOP pressure is 20 Hz below the frequency value measured at the known IOP pressure, then a value of 2 mmHg is subtracted from the known IOP pressure to generate the estimate of the unknown IOP pressure. To achieve a reasonable level of confidence in the estimate of the unknown IOP, it is preferred that the tonometer report to the patient only those extrapolated values that fall within a limited range about the known IOP pressure, such as 15 mmHg to 20 mmHg, and provide the indication "NORMAL" for extrapolated values that are below 15 mmHg, and the indication of "ABOVE NORMAL" for extrapolated values that are above 20 mmHg. As in the previous example, if the apparatus measures an undamped natural frequency that is above approximately 400 Hz, then there is a possibility of ambiguity, and the apparatus can output the following message to the patient of "PRESSURE OUT OF RANGE—SEE DOCTOR". It may be appreciated that the above number of 10 Hz per 1 mmHg change in IOP was provided for illustrative purposes only, and that the actual value may be different.

The above slope extrapolation process may also be done with the squares of the frequencies. A squared-frequency difference between the square of the first measured frequency value and the square of a first known value of the first vibratory frequency measured at a corresponding first known intraocular pressure is computed. This difference is then multiplied by a pre-computed slope factor which relates changes in intraocular pressure to changes in squared frequency values to generate a pressure differential. The estimate of the unknown intraocular pressure is then generated as the first known intraocular pressure plus the pressure differential.

These approaches may be implemented in the tonometers shown in FIGS. 4–6 by storing the known IOP pressure value, the corresponding value of the vibratory frequency of vibratory mode 1, and the extrapolation slope value in the "model memory" of the processor, and by having the estimation instruction set (stored in the instruction memory of the processor) direct the processor undertake the above comparison step and extrapolation step to generate an estimated pressure after the processor obtains the measured vibratory frequency at the unknown IOP pressure under the direction of the excitation instruction set and the monitor instruction set.

A further improved embodiment uses two frequency measurements of the lower vibratory mode of the patient's eye at two different known IOP values, which are preferably at least 3 mmHg apart in value. These two measurements are used to estimate a slope value that can be used in the above-described extrapolation processes. Each known IOP pressure value and its corresponding squared measured frequency form a point on an X-Y Cartesian graph of frequency versus pressure. The process to estimate the unknown IOP from its corresponding frequency measurement by extrapolation may be preformed relative to either of the two points at known IOP pressure values. For measured frequency values that fall between the two frequency values measured at known IOP values, either of the extrapolations provides an equivalent result to a standard two-point interpolation process. If the first measurement at a known IOP is made at 15 mmHg and the second is made at 20 mmHg, it is anticipated that an acceptable confidence level can be provided over a range from 13 mmHg to 22 mmHg. As a further refinement, the measured slope value may be compared to the value expected for the general human population to generate a confidence level in the accuracy of the measured results at the known IOP pressure values. If the measured slope value is too far different from the value expected for the general human population, it may be rejected and a new set of measurements may thereafter be obtained.

The interpolation/extrapolation process may be formulated in the following generalized manner. Equation [3] may be simplified to the following mathematical relationship:

$$(f_1)^2 = A_{0,1} + A_{1,1}\Delta p, \qquad [4]$$

and solved for the unknown pressure $\Delta p$:

$$\Delta p = [(f_1)^2 - A_{0,1}]/A_{1,1}, \qquad [5]$$

where $A_{0,1}$ and $A_{1,1}$ are constants related to the vibratory frequency. The frequency values measured at known IOP values may then be used to determine the constants $A_{0,1}$ and $A_{1,1}$ as follows:

$$A_{1,1} = [(f_{2,1})^2 - (f_{1,1})^2]/(\Delta p_2 - \Delta p_1), \text{ and} \qquad [6]$$

$$A_{0,1} = \tfrac{1}{2}[(f_{2,1})^2 + (f_{1,1})^2] - \tfrac{1}{2}(\Delta p_1 + \Delta p_2) \cdot A_{1,1}, \qquad [7]$$

where $f_{1,1}$ is the measured frequency value at a first known pressure value $\Delta p$, and $f_{2,1}$ is the measured frequency value at the second known pressure value $\Delta p_2$. The process represented by equation [4] and the values of constants $A_{0,1}$ and $A_{1,1}$ inherently performs the process of comparing the frequency value measured at the unknown IOP to the values measured at the known IOP to generate an estimate for the unknown IOP.

Further improved embodiments use additional measurements at known IOP pressures for determining values for $A_{0,1}$ and $A_{1,1}$, in which case a conventional linear least squares fitting process may be used to generate values of constants $A_{0,1}$ and $A_{1,1}$ from the measured data. Interpolation between the data points at known IOP values may also be used, with extrapolation being used at the end points.

These approach may be implemented in the tonometers shown in FIGS. 4–6 by storing the constants $A_{0,1}$ and $A_{1,1}$ in the "model memory" of the processor, and by having another set of instructions (called the "model instruction set", and stored in the instruction memory of the processor) that direct the processor to perform an evaluation of the function (e.g., mathematical relationship) of equation [5] using the stored constants $A_{0,1}$ and $A_{1,1}$ and an input vibratory frequency to provide a corresponding estimated pressure. The model instruction set is invoked by the above-described estimation instruction set, which provides to it the measured vibratory frequency. The model instruction set acting upon the stored model parameters thereby generates a pressure value as a function of the parameters $A_{0,1}$ and $A_{1,1}$ and an input frequency value for the vibratory mode. As shown in FIG. 1, the function provides a pressure value of zero for a non-zero input frequency value and a negative pressure value for a zero input frequency value, which is different from the characteristic of the conventional water-drop model of the eye.

Instead of storing the constants $A_{0,1}$ and $A_{1,1}$ in the model memory of the processor, the measured vibratory frequencies at the known IOP pressure values and the known pressure values themselves may be stored in the model memory, and the model instruction set may include instructions to generate constants $A_{0,1}$ and $A_{1,1}$ (according to equations [6] and [7]) when needed (so called "on-the-fly" computation). Furthermore, the vibratory frequencies may be stored in their standard form or their squared form, and each of these forms may be the actual values or difference values with respect to a reference frequency or as a difference with respect to one another. The pressure values may likewise be stored as the actual values, or as differences with respect to a pressure reference or as a difference between the pressure values. In general the data parameters in the model memory and the model instruction set may take any form which collectively produce a result which is mathematically equivalent to the form of equation [5] (equation [4] is one mathematical equivalent of equation [5]). Furthermore, the stored data parameters may be in encoded form (including compressed and encrypted forms) and the model instruction set may include instructions to decode the stored data parameters.

While the above embodiments have been described using the frequency measurements of the lower vibratory mode 1, it may be appreciated that other vibratory modes may be used in the above embodiments. For example, as mentioned above, the undamped natural frequency of the next-higher vibratory mode 2 can be clearly distinguished from those of the adjacent vibratory modes 1 and 3 in the IOP pressure range of 3 mmHg to 11 mmHg (corresponding to squared frequencies in the range of $0.16 \times 10^6$ to $0.46 \times 10^6$, and frequencies of 400 Hz to 680 Hz). However, using the vibratory frequency of the next higher vibratory mode 2 for IOP pressure values above 11 mmHg encounters an ambiguity since the frequencies of vibratory mode 2 measured at these levels overlap the frequencies of the next higher-order mode 3 measured at low values of IOP pressure of about 3 mmHg and above. The ambiguity can be resolved by using information from another mode (preferably the lower order mode 1) to verify that frequencies measured at unknown pressures are associated with the vibratory mode that is being utilized, in this case vibratory mode 2. The higher order modes 2, 3, etc. have larger slope values, which enables one to potentially obtain higher resolution in the interpolation/extrapolation process. The use of a higher-order mode may also be used in conjunction with the use of the lower-order mode in the following manner: when the extrapolation process based on the data from the lower vibrator mode 1 determines that the unknown IOP is below about 11 mmHg, measured data related to the next higher vibratory mode 2 may be used to estimate the unknown IOP in the pressure range of approximately 3 mmHg to approximately 11 mmHg, most likely with better resolution.

Multiple Vibratory Frequency Embodiments

The use of the higher order vibratory modes offers the potential of higher accuracy and resolution in the measurements of unknown IOP pressures, but, as indicated above, these higher order vibratory modes have overlapping frequency bands in the pressure range of interest, which leads to ambiguities. As a result, when a single vibratory frequency is measured at an unknown pressure, there usually is an uncertainty as to which vibratory mode it is associated with, unless the measured frequency is below approximately 400 Hz. In this section, we describe additional embodiments of the present invention which resolve this ambiguity.

The slopes of the lines shown in FIG. 1 for the higher order modes and their spacing with respect to one another may be used to resolve the ambiguities in the following manners. As an example, in FIG. 7, we show exemplary graphs the of the undamped natural frequencies of five adjacent vibratory modes 1–5, the first three modes 1–3 being previously shown in FIG. 1 and based on experimental data, and the last two modes (4 and 5) being projections for the next two higher modes which have been included to illustrate the following methods. Each line represent a function which relates a vibratory frequency to the eye's IOP pressure, and can be determined from one or more measure values of the corresponding undamped natural frequency at one or more corresponding known IOP pressures. Each of the lines can be defined by the mathematical relationships (i.e., functions) of equations [4] and [5], and equivalents thereof. We also show in FIG. 7 measurements of two undamped natural frequencies $f_A$ and $f_B$ obtained at an unknown IOP pressure value (approximately 870 Hz and 1300 Hz, respectively). Some measurement error is assumed to be in $f_A$ and $f_B$. Standing on its own, without any further information, measurement $f_A$ could be associated with any of vibratory modes 2, 3, and 4, which would imply the corresponding IOP pressure values of 20.6 mmHg, 10.2 mmHg, and 2.6 mmHg, respectively (as evaluated from the functions and their corresponding mathematical relationships). Associating measurement $f_A$ with vibratory mode 5 would imply a value of 0.8 mm Hg for the unknown IOP, which is not within a reasonably expected range. In a similar manner, measurement $f_B$ could be associated with any of vibratory modes 2–5, which would imply the corresponding IOP pressure values of 51 mmHg, 19.4 mmHg, 6.6 mmHg, and 5.6 mmHg, respectively. If it is known with reasonable certainty that measurements $f_A$ and $f_B$ are undamped natural frequencies of two adjacent vibratory modes, then one may examine tentative sets of mode assignments for the measurements $f_A$ and $f_B$, and then compute the unknown IOP values implied by the measurements and mode assignments of each set, as is done in Table. I:

TABLE I

| Set # | Mode Assignment $f_A$ | Mode Assignment $f_B$ | Implied IOPs (mm Hg) | Average IOP | Mean Deviation | Standard Deviation |
|---|---|---|---|---|---|---|
| 1 | 2 | 3 | 20.6 and 19.4 | 20 | 0.6 | 0.622 |
| 2 | 3 | 4 | 6.6 and 10.2 | 8.4 | 1.8 | 2.55 |
| 3 | 4 | 5 | 2.6 and 5.6 | 4.1 | 1.5 | 2.12 |
| 4 | 5 | — | 0.8 --- Out of reasonably expected pressure range. | | | |

Set #1 is graphically indicated in FIG. 7 at reference number 11, set #2 is graphically indicated at reference number 12, and set #3 is graphically indicated at reference number 13. From the implied IOP pressure values of each set, an average IOP value, a mean deviation, and a standard deviation can be computed for each set, as is shown in the last three columns of Table I. Of the two viable sets, set #1 of the mode assignments has the lowest mean deviation and standard deviation, and the average IOP value derived from this set has the highest probability of being the best estimate of the unknown IOP pressure. Greater certainty of this result can be obtained if the undamped natural frequency of the lower order mode 1 can be clearly obtained at the same unknown IOP pressure.

To improve the accuracy of the estimate, the above averaging process can be extended to obtain the measured undamped natural frequencies $f_C$, $f_D$, etc. of additional vibratory modes (such as mode #1 and #4, #5, etc.) and include their corresponding implied IOPs in the average and deviation calculations. In this regard, we note that computing an average IOP value for a set from the set's implied pressures using the formalism of the linear least squares process provides an equivalent result to that provided by the above averaging process. This is because the mathematical operations of the linear least squares process reduce down to those of the averaging process in the special case of where only one unknown is being solved for.

In some cases, there may not be a reasonable degree of certainty that the measurements $f_A$ and $f_B$ are undamped natural frequencies from adjacent vibratory modes; for example, $f_A$ may be associated with vibrator mode 2 and $f_B$ may be associated with vibratory mode 4. In such a case, it is relatively simple to extend the above method to include additional tentative sets to cover these possibilities, as shown in Table II with new sets #5, #6, and #7.

TABLE II

| Set # | Mode Assignment $f_A$ | Mode Assignment $f_B$ | Implied IOPs (mm Hg) | Average IOP | Mean Deviation | Standard Deviation |
|---|---|---|---|---|---|---|
| 1 | 2 | 3 | 20.6 and 19.4 | 20 | 0.6 | 0.622 |
| 2 | 3 | 4 | 6.6 and 10.2 | 8.4 | 1.8 | 2.55 |
| 3 | 4 | 5 | 2.6 and 5.6 | 4.1 | 1.5 | 2.12 |
| 4 | 5 | — | 0.8 --- Out of reasonably expected pressure range. | | | |
| 5 | 2 | 4 | 20.6 and 10.2 | 15.4 | 5.2 | 7.35 |
| 6 | 2 | 5 | 20.6 and 5.6 | 13.1 | 7.5 | 10.6 |
| 7 | 3 | 5 | 6.6 and 5.6 | 6.1 | 0.5 | 0.71 |

Each of sets #5 and #6 has a much greater mean deviation and standard deviation than the deviations of either of sets #1–#3, and therefore has a much less probability of being the unknown IOP pressure. However, the mean deviation and standard deviation of set #7 are close to those of set #1. When normalized to their average IOP, these deviations are actually larger than the normalized deviations of set #1 (8% and 12% versus 3% and 3.1%), and thus set #1 appears to be the most probable assignment of modes to $f_A$ and $f_B$, and the average pressure derived from set #1 has the greatest probability of being the closest to the actual IOP pressure of the eye.

In most cases, it will be known with a high degree of certainty from the measurement process whether or not the measured frequencies $f_A$ and $f_B$ are adjacent. Nonetheless, going through the above process of checking for the possibility that they are not (such as by examining sets #5–#7) serves as an important consistency check that can be used to further improve the confidence level of the estimation.

In each of the averaging processes described above, the implied IOP pressures that are averaged together for a set may be weighted on the basis of one or more external factors, such as factors which representative of the accuracy of the frequency measurement, and/or the value of frequency measurement itself, and/or the value of the implied IOP pressure value, etc.

Since each of the lines (i.e., functions and mathematical relationships) shown in FIGS. 1 and 7 has been derived from one or more measured frequency values at one or more corresponding known IOP pressures, the above-described methods inherently comprise the step of comparing the measured values of one or more vibratory frequencies at the unknown IOP pressure to known frequency values of the one or more vibratory frequencies at one or more known IOP pressures to estimate value of the unknown intraocular pressure.

The above-described multiple vibratory frequency embodiments may be implemented in the tonometers shown in FIGS. 4–6 by constructing the estimation instruction set to perform the about outlined steps. In this case, the model parameters are expanded to cover the additional vibratory frequencies. The model instruction set is invoked by the estimation instruction set to provide the implied pressure values, as needed by the estimation instruction set. The estimation instruction set is configured to perform the following tasks as described previously in greater detail:

to obtain multiple vibratory frequencies by invoking the excitation instruction set and the monitor instruction set, to construct two or more sets of mode assignments for the measured vibratory frequencies, to invoke the model instruction set a plurality of times to obtain the implied IOP values for each assignment set, to compute the average IOP and at least one deviation for each set, and to estimate the unknown IOP value as the average IOP value from the assignment set which has the lowest measure of deviation.

Each of these tasks is executed by a respective group of instructions. The estimation instruction set may further include a group of instructions which estimates the confidence of the estimated IOP by looking at the computed IOP value and the mean deviations of the assignment sets, and by outputting an indication to the patient of an indeterminate measurement result rather than outputting the estimated for the unknown IOP pressure.

Additional Methods

In the above embodiments, a measured value of a vibratory frequency at an unknown IOP pressure is compared to one or more measured values of the vibratory frequency measured at one or more corresponding known IOP pressures. While the comparison in these examples has focused on comparing the measured frequency values or the squares of the measured frequency values, it may be appreciated that the comparison may be accomplished in additional ways. For example, one may configure the tonometer (e.g., configure its excitation and monitor instructions sets) to obtain a segment of the frequency spectrum (amplitude plus phase) around each vibratory frequency as it is measured, both at the unknown IOP pressure and at the known IOP pressures. One may then correlate the frequency spectrum at the unknown IOP pressure value to each frequency spectrum at each known pressure value to determine a corresponding frequency offset. The frequency offset can then be used to determine if the unknown IOP pressure is above or below a known IOP pressure (e.g., if the frequency spectrum at the unknown IOP has to be shifted by the offset to higher frequencies to obtain a high correlation with the frequency spectrum at the known IOP, then the unknown IOP is less than the known IOP.) One may perform the correlation of the frequency spectrums with both the amplitude and the phase components of the frequency spectrums, or with just the amplitude components, or just with the phase components. To implement this method in any of the tonometers of the invention (e.g., FIGS. 4–6), representations of the segments of frequency spectrums measured at known IOP values are stored in the model memory, and the estimation instruction set is configured to undertake the above-described correlation of spectrums and determination of frequency offset.

As is known in the art, the correlation of the frequency spectrums may be done through the use of Fourier transform methods where the Fourier transforms of the frequency spectrums are processed to estimate the frequency offset. To implement this method in any of the tonometers of the invention (e.g., FIGS. 4–6), representations the segments of frequency spectrums measured at known IOP values are stored in the model memory, or representations of their Fourier transforms are stored, and the estimation instruction set is configured to undertake the above-described processing of Fourier transforms and determination of frequency offset.

As a further extension of these approaches, one may correlate the frequency spectrums of a vibratory frequency from two known IOP pressures to find a first frequency offset for the pressure difference between the two IOP pressures. A frequency spectrum of the vibratory frequency from an unknown IOP pressure may then be correlated against either of the previous spectrums to find a second frequency offset, and the unknown IOP pressure may be estimated through interpolation or extrapolation using the two frequency offsets and the known pressure values. In the tonometer, the model memory would also store representations of the additional frequency spectrums, and the estimation instruction set would be augmented accordingly.

Tonometer Calibration

Each of the above-described eye models stored in the processors requires one or more sets of one or more vibratory frequencies measured at corresponding known values of IOP, either are direct values or as frequency spectrums thereof. For those embodiments which only require a set of data parameters representative of a single vibratory frequency (or frequency spectrum therefor) measured at a single known IOP pressure value, the following calibration steps may be taken: the patient visits the doctor to have the IOP pressure of his/her eyes measured by the doctor by a conventional tonometer. Substantially at the same time, such as just before or just after the conventional tonometer measurement, the patient's eye's are scanned with an exemplary tonometer according to the present invention to find one or more vibratory frequencies (or frequency spectrums therefor), preferably including the vibratory frequency associated with the lower order mode 1. To do this, the doctor instructs the tonometer, via a human interface, to enter a special calibration mode. Either before or after the tonometer measures the vibratory frequencies, the doctor inputs the IOP pressure measurement obtained from the conventional tonometer as the "known IOP pressure" to the exemplary tonometer of the invention via the human interface. For those embodiments that employ slope extrapolation with one data point, the doctor may also enter a slope value for each eye. Thereafter, the exemplary tonometer of the invention is instructed to enter its measurement mode. The human interface may take the form of a key pad, or may take the form of a electrical cable interconnect (e.g., RS-232) to a computer which runs a software interface program.

For those embodiments which use two or more sets of data parameters (or segments of frequency spectrums), each set being representative of one or more vibratory frequencies measured at a known IOP pressure value, the above-described procedure may be extended to preformed the steps again at a different time where the patient's IOP value has changed, preferably by about 3 mmHg or more. Specifically, the patient' eye is measured a first time with a conventional tonometer, and then a second time with the conventional tonometer when the eye's IOP value is different from its value during the first measurement by about 3 mmHg or more. The patient's eye is measured with an exemplary tonometer of the invention to obtain a first set of one or more measured vibratory frequencies (or frequency spectrum segment(s)) of one or more corresponding vibratory modes, the measuring step being done at a time that is closer to the first time than the second time. This data and the corresponding known IOP value are entered into the exemplary tonometer of the invention as described above. The patient's eye is further measured with an exemplary tonometer of the present invention again to obtain a second set of one or more measured vibratory frequencies (or frequency spectrum segment(s)) of the corresponding one or more vibratory modes measured the first time, with the second measuring step being done at a time that is closer to the second time than the first time. This data and the corresponding known IOP value are entered into the exemplary tonometer of the invention as described above, and the tonometer is instructed to use the data parameters of the two sets.

FIG. 8 shows an embodiment of the present invention similar to the one shown in FIG. 5 (ultrasonic displacement detector) which can be used to measure the patient's eye at different atmospheric pressures at one sitting, thereby enabling the vibratory frequencies (or frequency spectrum segments therefor) of the patient's eyes to be measured at several IOP values. The embodiment shown in FIG. 8 is intended to be used in the doctor's office and comprises the same components as shown in FIG. 5, plus the following additional components:

1. A goggle pressure chamber for mounting against the patient's upper front face in the same manner as a water diving mask. An air-tight flexible pressure seal is disposed between the chamber and the patient's face, and fastening straps maintain the goggle pressure chamber against the patient's upper face. The exciter, ultrasonic emitter, ultrasonic detector, and illuminated target are disposed within the chamber, as seen within the cut-out section of the chamber, and are fastened to a wall of the chamber in a manner than enables the measurement of the eye.

2. An air compressor/vacuum pump having a pressure output coupled to an air pressure inlet of the goggle pressure chamber by an air hose. The pump can increase or decrease the pressure of the gaseous environment within the goggle pressure chamber relative to atmospheric pressure under the direction of the processor.

3. A pressure sensor within the goggle pressure chamber to measure the pressure inside the chamber for the processor.

4. An electrical cable which conveys control signals and power from the processor to the exciter, illuminated display, and ultrasonic emitter within the goggle chamber, and which conveys signals from the ultrasonic detector and the pressure sensor to the processor housing 60.

5. Further sets of instructions within the instruction memory which direct the processor to vary the pressure within the goggle chamber and make measurements of vibratory frequencies at different pressures.

The IOP of the patient's eye is decreased by increasing the pressure within the goggle chamber, and is increased by decreasing the pressure within the goggle chamber. A duplicate set of components may be included for the left eye, or the goggle may be rotated by 180-degrees. The doctor may first measure the patient's eye with a conventional tonometer at atmospheric pressure, and then use this embodiment to measure the vibratory frequencies of the patient's eye at atmospheric pressure. The doctor may then further use this embodiment to measure the patient's eye at various pressures relative to atmospheric pressure to obtain several sets of vibratory frequencies (or frequency spectrum segments thereof) at several corresponding IOP pressure values, as directed by the processor and as measured by the pressure sensor. This data may then be programmed into an exemplary tonometer of FIG. 5, which the patient uses at home.

While the present invention has been particularly described with respect to the illustrated embodiments, it will be appreciated that various alterations, modifications and adaptations may be made based on the present disclosure, and are intended to be within the scope of the present invention. While the invention has been described in connection with what is presently considered to be the most practical and preferred embodiments, it is to be understood that the present invention is not limited to the disclosed embodiments but, on the contrary, is intended to cover various modifications and equivalent arrangements included within the scope of the appended claims.

What is claimed is:

1. A method of estimating the intraocular pressure of an eye of a mammal with a gaseous environment around a portion of its surface, the gaseous environment having a pressure, the intraocular pressure being the difference between the pressure inside the eye and the pressure of the gaseous environment, said method comprising the steps of:
   (a) measuring a first frequency value of a first vibratory frequency of the eye at a portion of the sclera or cornea of the eye at an unknown intraocular pressure, said first vibratory frequency being associated with a corresponding first vibratory mode of the eye and having a value which varies as a first function of the eye's intraocular pressure, the first function having form which extends or extrapolates to a non-zero frequency value for a zero value of intraocular pressure and to a zero frequency value for a negative value of intraocular pressure; and
   (b) comparing the first measured frequency value to one or more known frequency values of the first vibratory frequency measured at corresponding known intraocular pressures to estimate value of the unknown intraocular pressure.

2. The method of claim 1 further comprising the steps of:
   (c) measuring a second frequency value of a second vibratory frequency of the eye at the portion of sclera or cornea of the eye at the unknown intraocular pressure value, said second vibratory frequency being associated with a corresponding second vibratory mode of the sclera and having a value which varies as a second function of the eye's intraocular pressure, the second function having form which extends or extrapolates to a non-zero frequency value for a zero value of intraocular pressure and to a zero frequency value for a negative value of intraocular pressure; and
   wherein step (b) comprises the step of comparing the first and second measured frequency values measured at the unknown intraocular pressure to the one or more known values of the first vibratory frequency, to the known intraocular pressures corresponding thereto, and to one or more known values of the second vibratory frequency measured at corresponding known intraocular pressures to estimate value of the unknown intraocular pressure.

3. The method of claim 2 wherein step (a) comprises the steps of:
   applying a plurality of vibrations at a plurality of frequencies to the eye, at least some of the vibrations causing one or more portions of the eye's surface to undergo an oscillatory motion;
   measuring the phase of the vibratory motion of a portion of the eye's surface relative to the applied vibrations; and
   selecting the first measured vibratory frequency as a first frequency of the applied vibrations at which the measured phase of the vibratory motion lags the phase of the applied vibrations by approximately 90 or 270 degrees; and
   wherein step (c) comprises the steps of:
      applying a plurality of vibrations at a plurality of frequencies to the eye, at least some of the vibrations causing one or more portions of the eye's surface to undergo an oscillatory motion;
      measuring the phase of the vibratory motion of a portion of the eye's surface relative to the applied vibrations; and
      selecting the second measured vibratory frequency as a second frequency of the applied vibrations at which the measured phase of the vibratory motion lags the phase of the applied vibrations by approximately 90 or 270 degrees.

4. The method of claim 2 wherein the first measured vibratory frequency and the second measured vibratory frequency differ from one other by at least 50 Hz.

5. The method of claim 1 wherein step (a) comprising the steps of:
   applying a plurality of vibrations at a plurality of frequencies to the eye, at least some of the vibrations causing one or more portions of the eye's surface to undergo an oscillatory motion;
   measuring the phase of the vibratory motion of a portion of the eye's surface relative to the applied vibrations; and
   selecting the first measured vibratory frequency as a first frequency of the applied vibrations at which the measured phase of the vibratory motion lags the phase of the applied vibrations by approximately 90 or 270 degrees.

6. The method of claim 1 wherein step (b) comprises the step of comparing the first measured frequency value to a first known value of the first vibratory frequency measured at a corresponding first known intraocular pressure and outputing an indication that the unknown pressure is above the first known intraocular pressure when the first measured frequency value is greater than the known value of the first vibratory frequency, and outputing an indication that the unknown pressure is below the first known intraocular pressure when the first measured frequency value is less than the known value of the first vibratory frequency.

7. The method of claim 1 wherein step (b) comprises the steps of:
   computing a frequency difference between the first measured frequency value and a first known value of the first vibratory frequency measured at a corresponding first known intraocular pressure;

generating a pressure differential by multiplying the difference by a pre-computed factor which relates changes in intraocular pressure to changes in frequency value; and generating the estimate of the unknown intraocular pressure as the first known intraocular pressure plus the pressure differential.

8. The method of claim 1 wherein step (b) comprises the steps of:

computing a squared-frequency difference between the square of the first measured frequency value and the square of a first known value of the first vibratory frequency measured at a corresponding first known intraocular pressure;

generating a pressure differential multiplying the squared-frequency difference by a pre-computed factor which relates changes in intraocular pressure to changes in squared frequency values; and generating the estimate of the unknown intraocular pressure as the first known intraocular pressure plus the pressure differential.

9. The method of claim 1 wherein step (b) comprises the steps of:

forming a mathematical relationship for the first vibratory mode which is mathematically equivalent to:

$$(f_1)^2 = A_0 + A_1 \Delta p,$$

where $f_1$ is an input frequency value of the mathematical relationship, where $\Delta p$ is the output pressure of the mathematical relationship, and where $A_0$ and $A_1$ are constants derived from the one or more known frequency values of the first vibratory frequency measured at the corresponding known intraocular pressures; and generating the estimate of the unknown intraocular pressure as being equal to $\Delta p$ from the mathematical relationship with $f_1$ being set equal to the first measured frequency value.

10. The method of claim 9 wherein the constants $A_0$ and $A_1$ are generated from a first measurement $f_{1,1}$ of the first vibratory frequency measured at a first known intraocular pressure $\Delta p_1$ and a second measurement $f_{2,1}$ of the first vibratory frequency measured at a second intraocular pressure $\Delta p_2$ according to forms which are mathematically equivalent to:

$$A_1 = [(f_{2,1})^2 - (f_{1,1})^2]/(\Delta p_2 - \Delta p_1), \text{ and}$$

$$A_0 = \frac{1}{2}[(f_{2,1})^2 + (f_{1,1})^2] - \frac{1}{2}(\Delta p_1 + \Delta p_2) \cdot A_{1,n}.$$

11. The method of claim 1 wherein step (a) comprises the step of measuring at least a portion of a first frequency spectrum of the measured portion of the eye, the portion including the first vibratory frequency, and wherein step (b) comprises the step of correlating the portion of the first frequency spectrum to a portion of a second frequency spectrum of the measured portion of the eye measured at a known value intraocular pressure and including the first vibratory frequency.

12. The method of claim 11 wherein the step of correlating comprises the steps of generating Fourier transforms of the portions of frequency spectrums.

13. A method of estimating the intraocular pressure of an eye of a mammal within a gaseous environment around a portion of the eye, the gaseous environment having a pressure, the intraocular pressure being the difference between the pressure inside the eye and the pressure of the gaseous environment, said method comprising the steps of:

(a) measuring a first vibratory frequency and a second vibratory frequency of an eye at an unknown intraocular pressure which is to be estimated to generate a first measured vibratory frequency and a second measured vibratory frequency, respectively;

(b) generating a first implied pressure value of the unknown intraocular pressure by comparing the first measured vibratory frequency to one or more measured values of a first previously-measured vibratory frequency measured at one or more corresponding known intraocular pressures;

(c) generating a second implied pressure value of the unknown intraocular pressure by comparing the second measured vibratory frequency to one or more measured values of a second previously-measured vibratory frequency measured at one or more corresponding known intraocular pressures;

(d) generating a third implied pressure value of the unknown intraocular pressure by comparing the first measured vibratory frequency to one or more measured values of the second previously-measured vibratory frequency;

(e) generating a fourth implied pressure value of the unknown intraocular pressure by comparing the second measured vibratory frequency to one or more measured values of a third previously-measured vibratory frequency measured at one or more corresponding known intraocular pressures;

(f) generating a first estimated pressure from the first and second implied pressure values as an average thereof, and generating a first deviation value representative of a deviation of the first and second implied pressure values from the first estimated pressure;

(g) generating a second estimated pressure from the third and fourth implied pressure values as an average thereof, and generating a second deviation value representative of a deviation of the third and fourth implied pressure values from the second estimated pressure; and wherein each of the vibratory frequencies has a value which varies as a respective function of the eye's intraocular pressure, each respective function extending or extrapolating to a non-zero frequency value for a zero value of intraocular pressure and to a zero frequency value for a negative value of intraocular pressure.

14. The method of claim 13 further comprising the step of selecting the first estimated pressure as a final estimated pressure if the first deviation value is less than the second deviation value, and the step of selecting the second estimated pressure as a final estimated pressure if the second deviation value is less than the first deviation value.

15. The method of claim 13 wherein the function of the first previously-measured vibratory frequency comprises a first mathematical relationship which provides an output pressure value for a corresponding input frequency value, wherein the function of the second previously-measured vibratory frequency comprises a second mathematical relationship which provides an output pressure value for a corresponding input frequency value, and wherein the function of the third previously-measured vibratory frequency comprises a third mathematical relationship which provides an output pressure value for a corresponding input frequency value;

wherein the step (b) of generating the first implied pressure value comprises evaluating the first mathematical relationship by providing the first measured vibratory frequency as the input frequency value of the first relationship and setting the first implied pressure value equal to the output pressure value of the first relationship, the first mathematical relationship being previously generated from at least the one or more values of the first previously-measured vibratory frequency;

wherein the step (c) of generating the second implied pressure value comprises evaluating the second mathematical relationship by providing the second measured vibratory frequency as the input frequency value of the second relationship and setting the second implied pressure value equal to the output pressure value of the second relationship, the second mathematical relationship being previously generated from at least the one or more values of the second previously-measured vibratory frequency;

wherein the step (d) of generating the third implied pressure value comprises evaluating the second mathematical relationship by providing the first measured vibratory frequency as the input frequency value of the second relationship and setting the third implied pressure value equal to the output pressure value of the second relationship; and wherein the step (e) of generating the fourth implied pressure value comprises evaluating the third mathematical relationship by providing the second measured vibratory frequency as the input frequency value of the third relationship and setting the fourth implied pressure value equal to the output pressure value of the third relationship, the third mathematical relationship being previously generated from at least the one or more values of the third previously-measured vibratory frequency.

16. The method of claim 15 wherein the mathematical relationships may be identified and distinguished with respect to one another by an index value n, wherein the n-th mathematical relationship comprises a form which is mathematically equivalent to:

$$(f_n)^2 = A_{0,n} + A_{1,n} \Delta p,$$

where $f_n$ is an input frequency value of the mathematical relationship, where $\Delta p$ is the output pressure of the mathematical relationship, and where $A_{0,n}$ and $A_{1,n}$ are constants related to the corresponding vibratory frequency.

17. The method of claim 16 wherein the constants $A_{0,n}$ and $A_{1,n}$ of an n-th relationship of a corresponding previously-measured vibratory frequency are generated from a first measurement $f_{1,n}$ of the corresponding vibratory frequency measured at a first known intraocular pressure $\Delta p_1$ and a second measurement $f_{2,n}$ of the corresponding vibratory frequency measured at a second intraocular pressure $\Delta p_2$ according to forms which are mathematically equivalent to:

$$A_{1,n} = [(f_{2,n})^2 - (f_{1,n})^2]/(\Delta p_2 - \Delta p_1), \text{ and}$$

$$A_{0,n} = \frac{1}{2}[(f_{2,n})^2 + (f_{1,n})^2] - \frac{1}{2}(\Delta p_1 + \Delta p_2) \cdot A_{1,n}.$$

18. The method of claim 13 wherein step (a) comprising the steps of:

applying a plurality of vibrations at a plurality of frequencies to the eye, at least some of the vibrations causing one or more portions of the eye's surface to undergo an oscillatory motion;

measuring the phase of the vibratory motion of a portion of the eye's surface relative to the applied vibrations;

selecting the first measured vibratory frequency as a first frequency of the applied vibrations at which the measured phase of the vibratory motion lags the phase of the applied vibrations by approximately 90 or 270 degrees; and selecting the second measured vibratory frequency as a second frequency of the applied vibrations at which the measured phase of the vibratory motion lags the phase of the applied vibrations by approximately 90 or 270 degrees.

19. The method of claim 13 wherein the first measured vibratory frequency and the second measured vibratory frequency differ from one another by at least 50 Hz.

20. A method of estimating the intraocular pressure of an eye of a mammal within a gaseous environment around a portion of its surface, the gaseous environment having a pressure, the intraocular pressure being the difference between the pressure inside the eye and the pressure of the gaseous environment, said method comprising the steps of:

(a) measuring, at an unknown intraocular pressure which is to be estimated, a plurality of vibratory frequencies of an eye to generate a plurality of measured vibratory frequencies;

(b) making an assignment of a selected number of the measured vibratory frequencies to corresponding selected ones of a plurality of mathematical relationships, each mathematical relationship being associated with a corresponding vibratory mode and corresponding vibratory frequency and providing an output pressure value for a corresponding input frequency value, each mathematical relationship being previously generated from at least one or more measured values of the corresponding vibratory frequency measured at one or more known intraocular pressures;

(c) computing a plurality of implied pressure values for the unknown intraocular pressure value, each implied pressure value being generated by providing the measured vibratory frequency previously assigned to the mathematical relationship as the input frequency value of the relationship and setting the implied pressure value equal to the output pressure value of the relationship; and (d) generating an average of the implied pressure values generated by step (c).

21. The method of claim 20 wherein step (d) further comprises the step of generating a corresponding deviation representative a deviation of the implied pressure values from the average; and wherein the method further comprises the step of repeating steps (b) through (d) one or more times, each time with a different assignment of measured vibratory frequencies, and generating the estimate for the unknown intraocular pressure as the average computed by step (d) which has the smallest corresponding deviation value.

22. The method of claim 20 wherein the mathematical relationships may be identified and distinguished with respect to one another by an index value n, wherein the n-th mathematical relationship comprises a form which is mathematically equivalent to:

$$(f_n)^2 = A_{0,n} + A_{1,n} \Delta p,$$

where $f_n$ is an input frequency value of the mathematical relationship, where $\Delta p$ is the output pressure of the mathematical relationship, and where $A_{0,n}$ and $A_{1,n}$ are constants related to the corresponding vibratory frequency.

23. The method of claim 22 wherein the constants $A_{0,n}$ and $A_{1,n}$ of an n-th relationship are generated from a first measurement $f_{1,n}$ of the corresponding vibratory frequency measured at a first known intraocular pressure $\Delta p_1$ and a second measurement $f_{2,n}$ of the corresponding vibratory frequency measured at a second intraocular pressure $\Delta p_2$ according to forms which are mathematically equivalent to:

$A_{1,n} = [(f_{2,n})^2 - (f_{1,n})^2]/(\Delta p_2 - \Delta p_1)$, and $A_{0,n} = \frac{1}{2}[(f_{2,n})^2 + (f_{1,n})^2] - \frac{1}{2}(\Delta p_1 + \Delta p_2) \cdot A_{1,n}$.

24. The method of claim 20 wherein step (a) comprising the steps of:
applying a plurality of vibrations at a plurality of frequencies to the eye, at least some of the vibrations causing one or more portions of the eye's surface to undergo an oscillatory motion;
measuring the phase of the vibratory motion of a portion of the eye's surface relative to the applied vibrations;
selecting two or more frequencies of the applied vibrations at which the measured phase of the vibratory motion lags the phase of the applied vibrations by approximately 90 or 270 degrees, each selected frequency being designated as a measured vibratory frequency.

25. The method of claim 20 wherein each of the measured vibratory frequencies differs from each of the other measured vibratory frequencies by at least 50 Hz.

26. The method of claim 20 wherein each of the vibratory frequencies has a value which varies as a respective function of the eye's intraocular pressure, each respective function extending or extrapolating to a non-zero frequency value for a zero value of intraocular pressure and to a zero frequency value for a negative value of intraocular pressure.

27. A method of measuring the intraocular pressure of a patient's eye with a first tonometer, the first tonometer having a model which estimates the pressure of an eye as a function of a set of one or more vibratory frequencies of the eye and a plurality of data parameters, the first tonometer having a first memory for storing the data parameters of the model, an ability to measure the patient's eye to obtain a set of one or more measured vibratory frequencies of one or more corresponding vibratory modes of the patient's eye, and an ability to provide a set of measured vibratory frequencies to the model to estimate the corresponding pressure of the eye, said method comprising the steps of:
(a) measuring the intraocular pressure of the patient's eye at a first time with a second tonometer that is different from the first tonometer, the measured pressure being designated as the first pressure;
(b) measuring the intraocular pressure of the patient's eye at a second time with the second tonometer or with a third tonometer that is different from the first tonometer, the measured pressure being designated as the second pressure and being different from the first pressure by an amount of three or more millimeters of Mercury;
(c) measuring the patient's eye with the first tonometer to obtain a first set of one or more measured vibratory frequencies of one or more corresponding vibratory modes, the measuring step being done at a time that is closer to the first time than the second time;
(d) measuring the patient's eye with the first tonometer to obtain a second set of one or more measured vibratory frequencies of said corresponding one or more vibratory modes, the measuring step being done at a time that is closer to the second time than the first time; and
(e) storing in the first memory a set of data parameters that is representative of the known intraocular pressures and the measured vibratory frequencies at the known intraocular pressures.

28. The method of claim 27 further comprising the steps of:
(f) measuring the patient's eye with the first tonometer to obtain a third set of one or more measured vibratory frequencies of said corresponding vibratory modes at an unknown intraocular pressure; and
(g) inputting the third set of one or more measured vibratory frequencies to the model to estimate the corresponding pressure of the patient's eye.

29. The method of claim 27 wherein step (e) comprises the step of computing at least one of the data parameters of the first tonometer's model from the first set of measured vibratory frequencies, the second set of measured vibratory frequencies, the first pressure, and the second pressure prior to storing said at least one of the data parameters in the first memory.

30. The method of claim 27 wherein step (e) comprises storing one of the intraocular pressures as one of the data parameters in the first memory.

31. The method of claim 27 wherein step (e) comprises storing one or more of the measured vibratory frequencies as one or more corresponding data parameters in the first memory.

32. The method of claim 27 wherein step (e) comprises storing one or more squared measured vibratory frequencies as one or more corresponding data parameters in the first memory.

33. The method of claim 27 wherein the corresponding vibratory modes of the first set of measure vibratory frequencies are the same as the corresponding vibratory modes of the second set of measured vibratory frequencies.

34. A method of measuring the intraocular pressure of a patient's eye with a first tonometer, the first tonometer having a model which estimates the pressure of an eye as a function of a set of two or more vibratory frequencies of the eye and a plurality of data parameters, the first tonometer further having a first memory for storing the data parameters of the model, an ability to measure the patient's eye to obtain a set of two or more vibratory frequencies of one or more corresponding vibratory modes of the patient's eye, and an ability to provide a set of vibratory frequencies to the model to estimate the corresponding pressure of the eye, said method comprising the steps of:
(a) directing the patient to have the intraocular pressure of his or her eye measured at a first time with a second tonometer which is different from the first tonometer, the measured pressure being designated as the first pressure;
(b) directing the patient to have the intraocular pressure of his or her eye measured at a second time with the second tonometer or with a third tonometer that is different from the first tonometer, the measured pressure being designated as the second pressure and being different from the first pressure by an amount of three (3) or more millimeters of Mercury;
(c) directing the patient to have his or her eye measured with the first tonometer to obtain a first set of vibratory frequencies of one or more corresponding vibratory modes, the measurement being done at a time which is closer to the first time than the second time;

(d) directing the patient to have his or her eye measured with the first tonometer to obtain a second set of vibratory frequencies of said corresponding one or more vibratory modes, the measurement being done at a time which is closer to the second time than the first time;

(e) providing a processor to generate the parameters of the first tonometer's model from the first set of vibratory frequencies, the second set of vibratory frequencies, the first pressure, and the second pressure;

(f) directing the patient to have the first and second pressures provided to the processor; and (g) directing the processor to generate the parameters of the first tonometer's model and to provide the generated parameters in the first memory.

35. The method of claim 34 further comprising the steps of:

(h) directing the patient to have his or her eye measured with the first tonometer to obtain a third set of vibratory frequencies; and (i) directing a processor within the first tonometer to estimate the pressure corresponding to the third set of vibratory frequencies from the tonometer's model and the third set of vibratory frequencies.

36. The method of claim 34 wherein the processor is external to the first tonometer.

37. The method of claim 34 wherein the processor is internal to the first tonometer and has a human interface that receives the values of the first and second pressures.

38. The method of claim 34 wherein step (g) generates one of the data parameters as the first pressure.

39. The method of claim 34 wherein step (g) generates one or more of the data parameters as one or more corresponding vibratory frequencies of the first set of vibratory frequencies.

40. A tonometer which measures the intraocular pressure of an eye of a mammal within a gaseous environment around a portion of its surface, the gaseous environment having a pressure, the intraocular pressure being the difference between the pressure inside the eye and the pressure of the gaseous environment, said tonometer comprising:

a processor having a first memory and a second memory;

a controllable frequency generator having a control input coupled to the processor and an output;

a vibratory exciter having an electric input coupled to the output of frequency generator and an output which delivers vibrations to the eye;

a displacement detector which detects vibratory displacements of a surface area of the eye, said displacement detector having an electrical output which provides a signal representative of the vibratory displacements;

a phase detector having a first input which receives a signal related to the output of the controlled frequency generator, a second input coupled to the electrical output of the displacement detector, and an output coupled to processor which provides a value related to the phase difference between the signals at the detector's first and second inputs;

a model of the pressure of the eye based on one or more vibratory frequencies of the eye, the model comprising a first set of instructions stored in said first memory, and a set of data parameters stored in said second memory for each vibratory frequency, the first set of instructions operating on the corresponding data parameters of a vibratory frequency to generate a pressure value as a function of the parameters and an input frequency value, each said function corresponding to a vibratory frequency and having form which extends or extrapolates to a non-zero frequency value for a zero value of intraocular pressure and to a zero frequency value for a negative value of intraocular pressure;

a second set of instructions stored in the first memory that directs the processor to command the controlled frequency generator to output a plurality of waveforms at a plurality of different frequencies;

a third set of instructions which directs the processor to monitor the output of the phase detector and to detect one or more vibratory frequencies therefrom; and a fourth set of instructions stored in the first memory that directs the processor to compute an estimated pressure from a set of detected vibratory frequencies and the model, the fourth set directing the processor to execute the first set of instructions using at least one set of stored parameters.

41. The tonometer of claims 40 wherein the function of each vibratory mode has a form which is mathematically equivalent to:

$$(f_{s,n})^2 = A_{0,n} + A_{1,n} \Delta p$$

where $f_{s,n}$ is a measured value of the vibratory frequency, where $\Delta p$ is the implied pressure value, where $A_{0,n}$ and $A_{1,n}$ are variable parameters, and where the index n identifies the vibratory mode; and wherein the first set of instructions generates a pressure value in a form which is mathematically equivalent to:

$$\Delta p = \{(f_{s,n})^2 - A_{0,n}\}/A_{1,n}.$$

42. The tonomoeter of claim 41 wherein the parameters of the model are derived from a first set ($f_{1,k}$) of vibratory frequencies measured at a first known pressure level of the eye and a second set ($f_{2,k}$) of vibratory frequencies measured at a second known and different pressure level of the eye from mathematical forms equivalent to:

$$A_{1,n} = [(f_{2,n})^2 - (f_{1,n})^2]/(\Delta p_2 - \Delta p_1)$$

$$A_{0,n} = \frac{1}{2} \cdot [(f_{2,n})^2 + (f_{1,n})^2] - \frac{1}{2}(\Delta p_1 + \Delta p_2) A_{1,n},$$

where $\Delta p_1$ and $\Delta p_2$ are the first and second pressures as referenced from atmospheric pressure.

43. The tonometer of claim 40 further comprising a pressure chamber adapted to be fit over at least a portion of the upper face of a patient to provide a gaseous environment around the eye which can be varied, wherein the exciter and displacement detector are disposed within the chamber.

44. The tonometer of claim 43 further comprising a compressor pump having an output coupled to sealed chamber.

45. The tonometer of claim 43 further comprising a vacuum pump having an output coupled to sealed chamber.

46. The tonometer of claim 41 wherein the first memory comprises a nonvolatile memory, and wherein the parameters $A_{0,n}$ and $A_{1,n}$ are computed and stored in the first memory, and thereafter called from the first memory as needed in computing a plurality of estimated pressure values.

47. The tonomoter of claim 40 wherein each of the vibratory frequencies is greater than 50 Hz.

48. The tonometer of claim 41 wherein the second memory comprises a nonvolatile memory, wherein the data parameters stored therein comprise the first and second sets of vibratory frequencies and the first and second known pressures, and wherein the first set of instructions comprising a subset of instructions which direct the processor to compute the parameters $A_{0,n}$ and $A_{1,n}$ as needed from the data stored in the non-volatile memory.

49. The tonometer of claim 40 wherein the displacement detector comprises an ultrasonic emitter and an ultrasonic detector.

50. The tonometer of claim 40 wherein the vibratory exciter comprises an acoustical speaker.

51. The tonometer of claim 40 wherein output of the frequency generator is swept in either the ascending direction or descending direction, up to a value of 4000 Hz.

\* \* \* \* \*

UNITED STATES PATENT AND TRADEMARK OFFICE
CERTIFICATE OF CORRECTION

PATENT NO. : 6,673,014 B2
DATED : January 6, 2004
INVENTOR(S) : Badehi et al.

It is certified that error appears in the above-identified patent and that said Letters Patent is hereby corrected as shown below:

Column 25,
Line 44, after "having" insert -- a --.
Line 52, after "estimate" insert -- a --.
Line 62, after "having" insert -- a --.

Column 26,
Line 6, after "estimate" insert -- the --.
Line 37, delete "other" and insert therefor -- another --.
Line 38, delete "comprising" and insert therefor -- comprises --.
Lines 56 and 59, delete "outputing" and insert therefor -- outputting --.

Column 27,
Line 17, after "differential" insert -- by --.
Line 60, after "value" insert -- of --.

Column 30,
Line 64, delete "$(f_n) =^2 A_{0,n} + A_{1,n} \Delta p$" therefor -- $(f_n)^2 = A_{0,n} + A_{1,n} \Delta p$ --.

Column 31,
Line 14, delete "comprising" and insert therefor -- comprises --.

Column 32,
Line 36, delete "measure" and insert therefor -- measured --.

Column 33,
Line 46, after "output of" insert -- the --.
Line 56, delete "coupled to processor" and insert therefor -- coupled to the processor --.

Column 34,
Line 3, after "having" insert -- a --.
Line 20, delete "claims" and insert therefor -- claim --.
Line 35, delete "tonomoeter" and insert therefor -- tonometer --.
Line 48, after "to" delete "be".
Lines 53 and 56, after "to" insert -- the --.

UNITED STATES PATENT AND TRADEMARK OFFICE
CERTIFICATE OF CORRECTION

PATENT NO. : 6,673,014 B2
DATED : January 6, 2004
INVENTOR(S) : Badehi et al.

It is certified that error appears in the above-identified patent and that said Letters Patent is hereby corrected as shown below:

Column 35,
Lines 2 and 3, delete "comprising" and insert therefor -- comprises --.

Signed and Sealed this

Twenty-eighth Day of December, 2004

JON W. DUDAS
*Director of the United States Patent and Trademark Office*